US008664255B2

(12) United States Patent
Freundlich et al.

(10) Patent No.: US 8,664,255 B2
(45) Date of Patent: Mar. 4, 2014

(54) INHIBITORS OF MYCOBACTERIUM TUBERCULOSIS MALATE SYNTHASE, METHODS OF MAKING AND USES THEREOF

(75) Inventors: Joel S. Freundlich, Princeton, NJ (US); James C. Sacchettini, College Station, TX (US); Inna V. Kriger, College Station, TX (US); Thomas R. Ioerger, College Station, TX (US); Vijay Gawandi, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 12/589,192

(22) Filed: Oct. 20, 2009

(65) Prior Publication Data

US 2010/0113477 A1 May 6, 2010

Related U.S. Application Data

(60) Provisional application No. 61/196,755, filed on Oct. 20, 2008.

(51) Int. Cl.

*A61K 31/121* (2006.01)
*C07C 49/215* (2006.01)
*C07C 49/217* (2006.01)
*C07D 207/12* (2006.01)
*C07D 233/64* (2006.01)

(52) U.S. Cl.

USPC ........... 514/399; 514/425; 514/545; 514/570; 548/333.5; 548/530; 568/303

(58) Field of Classification Search

USPC ................ 548/333.5, 530; 544/335; 546/314; 549/70, 488; 568/303

See application file for complete search history.

(56) References Cited

FOREIGN PATENT DOCUMENTS

| | | |
|---|---|---|
| EP | 1142872 A1 | 10/2001 |
| WO | WO 99/62513 | 12/1999 |
| WO | WO 99/62520 | 12/1999 |
| WO | WO 99/62897 | 12/1999 |
| WO | WO 2007/075896 | 7/2007 |

OTHER PUBLICATIONS

Jette, et al. Document No. 147:407090 (Sep. 27, 2007) retrieved from CAPLUS.*
Kawasuji, et al. Bioorg. Med. Chem. 14 (2006) 8430-8445.*
Cow, et. al. Document No. 145:230633 (Aug. 10, 2006) retrieved from CAPLUS.*
Garvey, et al. Document No. 140:157441 (Feb. 4, 2004) retrieved from CAPLUS.*
Pinto, et al. Document No. 138:287666 (Apr. 3, 2003) retrieved from CAPLUS.*
Kiyama, et al. Document No. 138:204936 (Feb. 27, 2003) retrieved from CAPLUS.*
Yersinia Pestis [online] retrieved from the internet on Feb. 28, 2013, URL; http:www.intelihealth.com/IH/ihtPrint/WSIHW000/9339/24674.html.*
Dunn, et al. Microbiology (2009), 155, 3166-3175.*
Cano, et al. Discovery of 1,1-Dioxo-1,2,6-thiadiazine-5-carboxamide Derivatives as Cannabinoid-like Molecules with Agonist and Antagonist Activity; *Bioorganic & Medicinal Chemistry*, 2007, vol. 15, No. 23, pp. 7480-7493.
Kim, J. et al. A Structures-Based 3D-QSAR(CoMSIA) Study on a Series of Aryl Diketoacids (ADK) as Inhibitors of HCV RNA-Dependent RNA Polymerase; *Bulletin of the Korean Chemical Society*. 2006, vol. 27, No. 11, pp. 1919-1922.
Sechi, M. et al. Form Ligand to Complexes: Inhibition of Human Immunodeficiency Virus Type 1 Integrase by β-Dikeo Acid Metal Complexes; *Journal of Medicinal Chemistry*, 2006, vol. 49, No. 14; pp. 4248-4260.
Nakayama, G, et al. A Fluorescence Polarization Assay for Screening Inhibitors Against the Ribonuclese H Activity of HIV-1 Reverse Transcriptase; *Analytical Biochemistry*, 2006, vol. 351, No. 2; pp. 260-265.
Wei, et al. Design, Synthesis, and Preliminary Biological Evaluation of Novel Ethyl 1-(2'Hydroxy-3'-Aroxypropl)-3Aryl-1H-Pyrazole-5-Carboxylate; *Bioorganic & Medicinal Chemistry Letters*, 2006, vol. 16, No. 24, pp. 6342-6347.
Di Santo, et al. Simple but Highly Effective Three-Dimensional Chemical-Feature-Based Pharmacophore Model for Diketo Acid Derivatives as Hepatitis C Virus RNA-Dependent RNA Polymerase Inhibitors; *Journal of Medicinal Chemistry*, 2005, vol. 48, No. 20, pp. 6304-6314.
Singh, S.K. et al. Synthesis and SAR/3D-QSAR Studies on the COX-2 Inhibitory Activity of 1,5-Diarylpyrazoles to Validate the Modified Pharmacophore; *European of Medicinal Chemistry*, 2005, vol. 40, No. 10, pp. 977-990.
Tumey, L. N. et al. The Identification and Optimization of 2,4-Diketobutyric Acids as Flap Endonuclease 1 Inhibitors; *Bioorganic & Medicinal Chemistry Letters*, 2004, vol. 14, No. 19, pp. 4915-4918.

(Continued)

*Primary Examiner* — Shawquia Young
(74) *Attorney, Agent, or Firm* — Benjamin Aaron Adler

(57) ABSTRACT

The present invention provides aryl- or heteroaryl-diketo acid compounds effective to inhibit an activity of a Mycobacterial malate synthase enzyme or to inhibit a malate synthase activity in other bacteria having the enzyme. The compounds may be phenyl- naphthyl-, or thienyl-substituted diketo acids and carboxylate derivatives thereof. Also provided are methods of treating tuberculosis or other pathophysiological conditions associated with a malate synthase enzyme with the inhibitory compounds and methods of in silico design of the inhibitory compounds. In addition, the present invention provides the inhibitory compounds designed by this method. Furthermore, three-dimensional X-ray crystal structures of the Mycobacterial malate synthase complexed with the inhibitory compounds are provided. Further still a method for stabilizing an aromatic or heteroaromatic diketo acid or its prodrug or close analog in solution by derivatizing at least the ortho position on the aromatic ring is provided.

12 Claims, 7 Drawing Sheets

(56) References Cited

OTHER PUBLICATIONS

Summa, V. et al. Discovery of α,γ-Diketo Acids as Potent Selective and Reversible Inhibitors of Hepatitis C Virus NS5b RNA-Dependent RNA Polymerase; *Journal of Medicinal Chemistry*, 2004, vol. 47, No. 1, pp. 14-17.

Braga, R. et al. Slow-Binding Inhibition of 2-Keto-3-Deoxy-6-Phosphogluconate (KDPG) Aldolase; *Bioorganic & Medicinal Chemistry Letters*, 2004, vol. 12, No. 11, pp. 2965-2972.

Maurin, C. et al. Improved Preparation and Structural Investigation of 4-aryl-4-oxo-2-hydroxy-2-butenoic Acids and Methyl Esters; *Tetrahedron*, 2004, vol. 60, No. 31, pp. 6479-6486.

Rubtsov, A. E. et al. Synthesis and Intramolecular Cyclization of N-Substituted 2-Amino-4-Aryl-4-oxo-2-Butenoic Acids; *Russian Journal of Organic Chemistry*, 2003, vol. 39, No. 6, pp. 869-874.

Wai, et al. 4-Aryl-2,4-Dioxobutanoic Acid Inhibitors of HIV-1 Integrase and Viral Replication in Cells; ; *Journal of Medicinal Chemistry*, 2000, vol. 43, No. 26, pp. 4923-4926.

Zhang, J. et al. Potent Nonpeptide Endothelin Antagonists: Synthesis and Structure-Activity Relationships of Pyrazole-5-Carboxylic Acids; *Bioorganic & Medicinal Chemistry Letters*, 2000, vol. 22, No. 22, pp. 2575-2578.

Igidov, N.M. et al. 1, 3, 4, 6-Tetracarbony Compounds. 3. Systhesis, Structural Features, and Antimicrobial Activity of 1, 6-Diaryl-3, 4-Dihydroxy-2 4-Hexadiene-1, 6-Diones; *Chemistry of Heterocyclic Compounds*, 1999, vol. 35, No. 11, pp. 1276-1285.

Milyutin, A. V. et al. Synthesis and Antiphlogistic and Analgesic Activities of 6-Methyl (phenyl)-3-(Aroylmethylene)-2-piperazin-2-Ones; *Khimiko-Farmatsevticheskii Zhurnal*, 1998, vol. 32, No. 1, pp. 27-29.

Kolotova, N.V. et al. Reaction of Aroylpyruvic Acids and Their Derivatives with (0-aminopheyl) Diphenylmethanol in the Snthesis of Pharmacologically Active Compounds; *Khimiko-Farmatsevticheskii Zhurnal*, 1998, vol. 32, No. 9, pp. 32-35.

Gein, V.L. et al. Synthesis and Antibacterial Activity of 1-Substituted 5-Aryl-4-Aroyl—3-Hydroxy-3-Pyrrolin-2-Ones; *Pharmaceutical Chemistry Journal*, 1997, vol. 31, No. 11, pp. 603-605.

Penning, T.D. et al. Synthesis and Biological Evaluation f the 1, 5-Diarylpyrazole Class of Cyclooxygenase-2 Inhibitors: Identification of 4-[5-(4-Methylphenyl)-3-(Trilluoomethyl)-1H-Pyrazol-1-yl]benzenesulfonamide (SC-58635, Celecoxib); *Journal of Medicinal Chemistry*, 1997, vol. 40, No. 9, pp. 1347-1365.

Igidov, N.M. et al. Amides and Hydrazides of Acylpyruvic Acids. 4. Synthesis and Pharmacological Activity of Some Amides of Aroyl- and Pivalol Pyruvic Acids; *Khimiko-Farmatsevticheskii Zhurnal*, 1996, vol. 30, No. 11, pp. 21-25.

Iwanami, Y. et al. *Heterocycles Structurally Influenced by a Side Chain. 11. 7-Phenacylxathopterins and 6-Phenacylisoxanthopterins*; Bulletin of the Chemical Society of Japan, 1972, vol. 45, No. 9, pp. 2829-2934.

Burch, H. A. et al. Acylpyruvates as Potential Antifungal Agents; *Journal of Medicinal Chemistry*, 1972, vol. 15, No. 4, pp. 429-431.

Kurkovskaya, L. N. et al. Intramolecular Hydrogen Bonding f Carbalkoxyl Derivatives of β-Dicarbonyl Compounds Studied by PMR Method; *Zhurnal Strukturnoi Khimii*, 1972, vol. 13, No. 6, pp. 1026-1032.

Mustafa A. et al. Experiments with Furochromones. Synthesis of Ammiol and Khellol; *Journal of Organic Chemistry*, May 18, 1960, vol. 26, pp. 886-890.

Schonberg, A. et al. Khellin and Allied Compounds; *Journal of the American Chemical Society*, 1950, vol. 72, pp. 1611-1617.

* cited by examiner

INHIBITORS OF MYCOBACTERIUM TUBERCULOSIS MALATE SYNTHASE, METHODS OF MAKING AND USES THEREOF

CROSS-REFERENCE TO RELATED APPLICATIONS

This nonprovisional application claims benefit of priority under 35 U.S.C. §119(e) of provisional application U.S. Ser. No. 61/196,755, filed Oct. 20, 2008, now abandoned, the entirety of which is hereby incorporated.

BACKGROUND OF THE INVENTION

1. Field of the Invention

The present invention relates generally to the fields of tuberculosis treatment, enzymology and drug screening. More specifically, the present invention relates to substituted aryl- and heteroaryldiketo acids and derivatives thereof as therapeutics in the treatment of tuberculosis, particularly persistent tuberculosis, and their design.

2. Description of the Related Art

Despite the discovery of streptomycin and several other outstanding anti-tubercular drugs in the 1950's, *Mycobacterium tuberculosis* (Mtb) continues to cause more deaths worldwide than any other infectious disease. Approximately one-third of the world's population is infected with Mtb, and 8 to 10 million new cases of TB are reported each year. Tuberculosis is estimated to kill about 2 to 3 million people each year, and these deaths are primarily associated with the poor of developing countries.

Mtb is an airborne threat that can be spread by coughs, sneezes, and even droplets from normal speech. In areas of high population density, TB can be spread very rapidly. TB infection rates are on the rise due in part to the HIV epidemic, as there is a synergistic relationship between HIV and TB, where both diseases progress much faster in the co-infected individual. TB has become the leading cause of death for people with HIV (13% of deaths worldwide).

While many new drugs discovered over the following 20 years showed tremendous promise for TB chemotherapy, reports of drug resistance invariably followed shortly after their introduction to the market. Chemotherapy for TB now uses a treatment of multiple antibiotics, e.g., isoniazid, pyrazinamide, ethambutol, and rifampin, that lasts between 6 to 12 months for drug sensitive infection. One major obstacle in combating Mtb during the course of the treatment is the bacteria's ability to survive for extended periods of time in the body in a non-replicative state, referred to as the persistent phase of infection. During this time, the bacteria are characterized as being recalcitrant to treatment by conventional anti-TB drugs and are able to evade the host immune response. This phenotypic resistance dictates the requirement for prolonged drug treatments and oftentimes results in patient non-compliance.

Another threat to the global control of TB is the asymptomatic latent infection. Asymptomatic infections can be activated unpredictably, especially if the patient becomes immunocompromised. The degree of similarity in the metabolic state between bacilli in the persistent and latent phases is not known. However, it is this inherent aspect of the bacteria—its ability to survive in the body for extended periods of time-which reduces the efficacy of current treatments. Drug-resistant strains to at least one TB drug have been found in every country in the world. Many factors contribute to the rise of drug resistance, including low compliance with therapy regimens, poor quality or counterfeit drugs, improper use of drugs, and inadequate health care systems.

In mycobacteria, persistence appears to involve a switch of metabolism to the glyoxylate shunt, which facilitates a metabolic shift in the carbon source to the acetyl CoA generated by the β-oxidation of fatty acids. The glyoxylate shunt enzymes isocitrate lyase (ICL) and malate synthase have been implicated as virulence or persistence factors in several different pathogens. Two genes of the glyoxylate shunt, icl1 and mls1, encoding isocitrate lyase and malate synthase, respectively, were induced upon phagocytosis of *Candida albicans* by macrophages. A mutant of *C. albicans* lacking icl1 was less virulent in mice than wild-type. The glyoxylate pathway has also been implicated in the pathogenesis of *Brucella abortus* and *Rhodococcus equi*, as well as in the virulence of the plant pathogens *Rhodococcus fascians* and *Stagonospora nodorum*.

For Mtb, it has been reported that genes encoding both of the enzymes are up-regulated in response to phagocytosis. Two genes encode for ICL enzymes in Mtb: icl1 and icl2. While the primary substrate for icl1 is isocitrate, it also possesses a methyl-isocitrate lyase activity, part of a distinct pathway, though some evidence exists for a partial overlap in functionality. An icl1 null strain of Mtb is able to establish an acute infection in mice, but is not able to sustain the chronic, persistent infection seen in mice infected with wild-type Mtb. Moreover, bacteria lacking both icl1 and icl2 are unable to grow on fatty acids or in macrophages, and are rapidly cleared from the lungs of infected mice. It has been reported that antibodies to malate synthase were found in 90% of patients during incipient subclinical tuberculosis. As neither of the genes encoding enzymes in the glyoxylate shunt are found in mammals, both MS and ICL have become targets for the design of drugs.

The anaplerotic maintenance of the tricarboxylic acid (TCA) cycle is afforded by the glyoxylate shunt during conditions where the generation of pyruvate from glycolysis is reduced and beta-oxidation of fatty acids provides the major source of carbon. This metabolic perturbation is vital to the survival of the bacteria. Beta-Oxidation of fatty acids results in increased levels of acetyl CoA, which gets incorporated into isocitrate. ICL converts isocitrate to glyoxylate and succinate. The next enzyme in the glyoxylate cycle, malate synthase, condenses glyoxylate and acetyl CoA to produce malate. An advantage of the glyoxylate cycle, during conditions where beta-oxidation is high, is the bypass of the $OO_2$—generating steps of the TCA cycle. When working in concert with the TCA cycle, the glyoxylate shunt will replenish the concentration of two intermediates, succinate and malate, which will have the overall effect of maintaining oxaloacetate levels (as the entry point for acetyl CoA in the TCA cycle).

In the Mtb genome, a single malate synthase gene (called glcB or mls1) encodes a malate synthase isoform (malate synthase G, Rv1837c). Malate synthase is an 80 kDa (741 amino acids) monomeric protein, homologous to malate synthase (AceB) of the gram-positive bacterium *Corynebacterium glutamicum* (Reinscheid et al. 1994) and the gram-negative *Escherichia coli*, with ~60% sequence identity. Functional properties of malate synthase from Mtb have been studied as well. The specific activity of the purified enzyme was 6 μmol/min/mg protein. The $K_m$ of the recombinant protein was determined to be 57 μM for glyoxylate and 30 μM for acetyl CoA. In the absence of divalent cations only negligible activity was measured for the purified enzyme. $Mg^{+2}$ at 5 mM was found to be the most effective cation. $Mn^{+2}$ was able to replace $Mg^{+2}$, yielding 40% of the activity obtained with $Mg^{+2}$. $Co^{+2}$, $Fe^{+2}$, $Ca^{+2}$, $Ba^{+2}$, $Ni^{+2}$, $Cd^{+2}$, $Zn^{+2}$, $Cu^{+2}$, and $Hg^{+2}$ were unable to support significant activity. The optimal pH for malate synthase activity was found to be 7.5. (Smith et al. 2003).

Also, the inhibition of Mtb malate synthase activity by several compounds, known to be effective against malate synthases, was examined. Oxalate, phosphoenolpyruvate, and bromopyruvate were the most potent inhibitors with inhibition constants of 400, 200, and 60 μM, respectively. Malate was shown to inhibit the activity to ~50% at 1 mM concentration. 3-Phosphoglycerate, 6-phosphogluconate, fructose-1,6-bisphosphate, and malonic acid had no inhibitory effect at relevant concentrations. Glycolate showed inhibition only at fairly high concentrations ($K_i$ of 900 μM), which is in contrast to other malate synthases such as the enzyme from *C. glutamicum*, which has a $K_i$ of 440 μM.

Thus, there is a recognized need in the art for tuberculosis drugs effective to treat persistent strains of *Mycobacterium tuberculosis*. Specifically, the prior art is deficient in novel substituted aryl- and heteroaryldiketo acids and derivatives thereof in the treatment of tuberculosis. The present invention fulfills this long-standing need and desire in the art.

SUMMARY OF THE INVENTION

The present invention is directed to a substituted diketo acid compound having the chemical structure comprising:

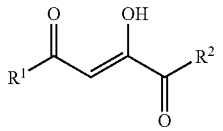

wherein $R^1$ is a phenyl, a naphthyl, a thienyl, bithiophenyl, imidazolyl, benzothienyl, furanyl, benzofuranyl, pyrimidinyl, pyrrolyl, or pyridyl or substituted derivatives thereof; and $R^2$ is H, OH, $OC_{1-6}$ alkyl, $NH_2$, $NHC_{1-6}$alkyl, or $N(C_{1-6}\ alkyl)_2$; or a pharmacologically acceptable salt thereof. Further to this embodiment there is provided a pharmaceutical composition comprising the aryl diketo acid compounds described supra and a pharmaceutically acceptable carrier.

The present invention also is directed to a substituted diketo acid comprising compounds listed in Example 3.

The present invention is directed further to a method for inhibiting an activity of a malate synthase enzyme in a bacterium, for example a *Mycobacterium*. The method comprises contacting the bacterium with an effective amount of one or more of the aryl diketo acid compounds described herein.

The present invention is directed further still to a method for treating tuberculosis in a subject. The method comprises administering one or more times a pharmacologically effective amount of one or more of the aryldiketo acid compounds described herein. Also, the present invention is directed to a related method comprising a further step of administering one or more times a pharmacologically effective amount of one or more other tuberculosis drugs.

The present invention is directed further still to a method for treating a pathophysiological condition caused by a bacterium having a malate synthase activity in a subject. The method comprises administering one or more times a pharmacologically effective amount of one or more of the aryldiketo acid compounds described herein. Also, the present invention is directed to a related method comprising a further step of administering one or more times a pharmacologically effective amount of one or more other drugs effective to treat the pathophysiological condition.

The present invention is directed further still to a method for designing a potential inhibitory compound of a *Mycobacterium* malate synthase enzyme. The method comprises identifying a compound in silico that interacts with the malate synthase active site screening the potential compound for inhibition of CoA production by Mycobacterial malate synthase. The identification is based at least in part on a computer model of a crystalline structure of the malate synthase enzyme. Also, the present invention is directed to a related method comprising the further step of measuring growth inhibition of a *Mycobacteria* culture in the presence of the screened inhibitory compound compared to growth of a control in the absence thereof.

The present invention is directed further still to an inhibitory compound designed by the method described herein.

The present invention is directed further still to a three-dimensional X-ray crystal structure comprising a Mycobacterial malate synthase complexed to an inhibitory compound designed by the method described herein.

The present invention is directed further still to a method for increasing the stability of an aromatic or heteroaromatic diketo acid compound in solution. The method comprises derivatzing the aromatic ring or heteroaromatic ring comprising the diketo acid or a prodrug thereof in at least an ortho position with a substituent effective to disrupt coplanarity of the aromatic or heteroaromatic ring with the diketo acid moiety thereby stabilizing the aromatic or heteroaromatic diketo acid compound.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
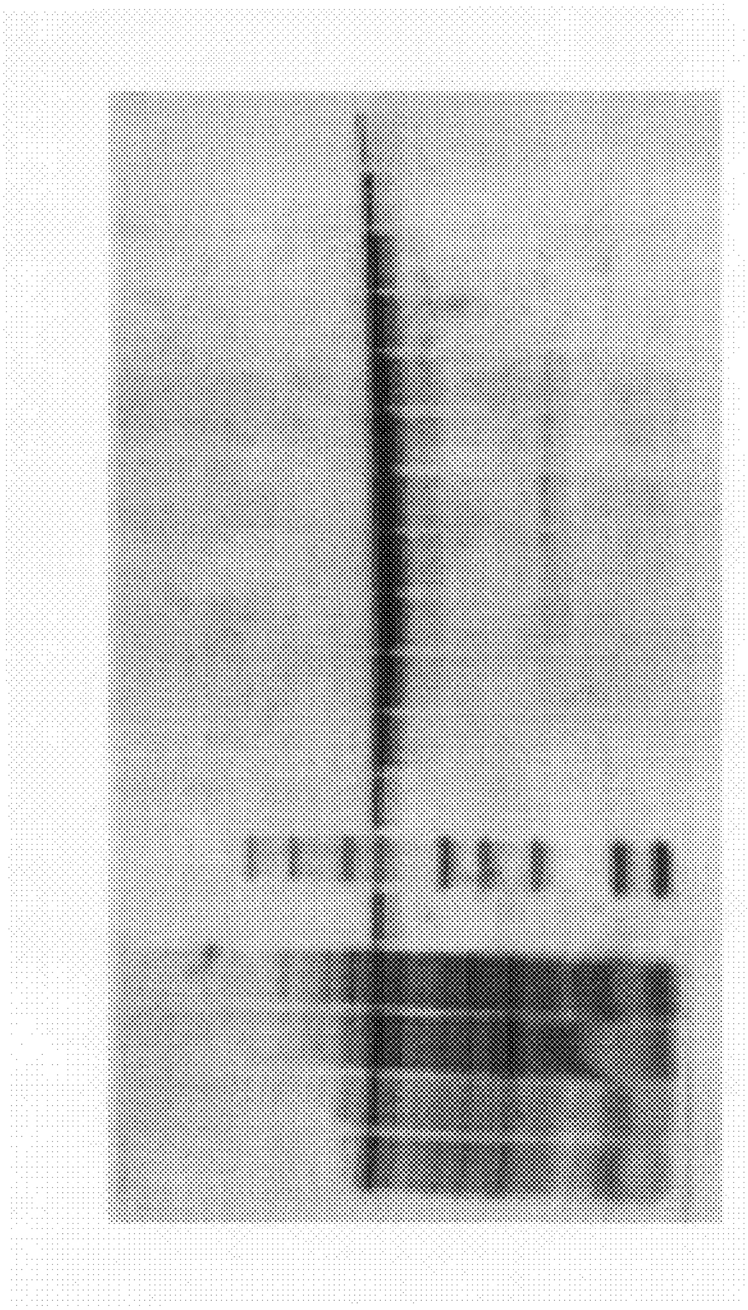
FIG. 1 is a gel depicting purification of the truncated form of Mtb malate synthase. Lane 6 is markers; lanes 7-18 are fractions from a gel filtration column showing greater than 95% pure malate synthase (80 kDa).

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "compound" is interchangeable with "inhibitor", or "inhibitory compound" and means a molecular entity of natural, semi-synthetic or synthetic origin that blocks, stops, inhibits, and/or suppresses substrate interactions with a Mycobacterial malate synthase, particularly the formation of CoA from acetyl CoA.

As used herein, the term "inhibit" refers to the ability of the compound to block, partially block, interfere, decrease, reduce or deactivate a Mycobacterial or other bacterial malate synthase enzyme or protein. Thus, one of skill in the art understands that the term inhibit encompasses a complete and/or partial loss of activity of a malate synthase. For example, a complete and/or partial loss of activity of the malate synthase may be indicated by a reduction in production of CoA, a reduction in mycobacterial cell proliferation, or the like.

As used herein, the term "contacting" refers to any suitable method of bringing one or more of the compounds described herein or other inhibitory agent into contact with a Mycobacterial or other bacterial malate synthase protein or polypeptide or fragment thereof or a *Mycobacterium* or other bacterium comprising the same. In vitro or ex vivo this is achieved by exposing the malate synthase protein or polypeptide or fragment thereof or cells comprising the same to the inhibitory agent in a suitable medium. For in vivo applications, any known method of administration is suitable as described herein.

As used herein, the terms "effective amount" or "pharmacologically effective amount" are interchangeable and refer to an amount that results in an improvement or remediation of the disease, such as tuberculosis. Those of skill in the art understand that the effective amount may improve the patient's or subject's condition, but may not be a complete cure of the disease and/or condition.

As used herein, the terms "treating" or "treatment" includes prophylactic treatment as well as alleviation of ongoing or intermittent symptoms occurring in a tuberculosis or persistent tuberculosis or other bacterial infection.

As used herein, the term "subject" refers to any target of the treatment.

In one embodiment of the present invention there is provided substituted diketo acid compound having the chemical structure comprising:

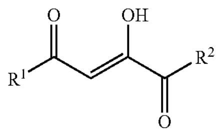

wherein $R^1$ is a phenyl, a naphthyl, a thienyl, bithiophenyl, imidazolyl, benzothienyl, furanyl, benzofuranyl, pyrimidinyl, pyrrolyl, or pyridyl or substituted derivatives thereof; and $R^2$ is H, OH, $OC_{1-6}$ alkyl, $NH_2$, $NHC_{1-6}$alkyl, or $N(C_{1-6}$ alkyl$)_2$; or a pharmacologically acceptable salt thereof. Further to this embodiment there is provided a pharmaceutical composition comprising the substituted diketo acid compounds described supra and a pharmaceutically acceptable carrier.

In both embodiments $R^1$ may be a phenyl substituted with one or more of $R^3$ at C2, $R^4$ at C3, $R^5$ at C4, $R^6$ at C5, or $R^7$ at C6 or a 1- or 2-naphthyl substituted with one or more of $R^3$ at C3, $R^4$ at C4, or $R^5$ at C5. For example, $R^3$, $R^4$, $R^5$, $R^6$, and $R^7$ independently may be H, OH, $NO_2$, $C_{1-6}$alkyl, $C_{1-6}$alkoxy, $O(C_{1-6}$alkyl$)O(C_{1-6}$alkyl), Br, F, Cl, I, Ph, $PhCH_2$, $PhOCH_3$, $Ph(CH_2)_2$, $CF_3$, $CH_3SO_2$, or imidazolyl. Particularly, one or more of $R^3$, $R^4$, $R^5$, $R^6$ or $R^7$ independently may be methoxy, Br, F, Cl, I, or methyl and $R^2$ may be OH or $OC_{1-6}$ alkyl. Also, in both embodiments $R^1$ may be 1- or 2-naphthyl, $R^2$ may be OH or $OC_{1-6}$ alkyl, $R^3$ and $R^4$ may be H, and $R^5$ may be $OC_{1-6}$ alkoxy. In addition, $R^1$ may be a 2- or 3-thienyl or (3-methyl)-2-thienyl substituted with of $R^8$ at C5, wherein $R^8$ is p-$R^3$Ph, phenoxyphenyl, or 2-thienyl.

In another embodiment of the present invention there is provided a substituted diketo acid compound with a chemical name shown in Example 3.

In another embodiment the present invention provides a method for inhibiting an activity of a malate synthase enzyme in a bacterium, comprising contacting a bacterium with an effective amount of one or more of the aryldiketo acid compound as described supra. In this embodiment, the bacterium may be a *Mycobacterium*. An example is *Mycobacterium tuberculosis*.

In yet another embodiment, the present invention provides a method for treating tuberculosis in a subject, comprising administering one or more times a pharmacologically effective amount of the inhibitor described supra to the subject. Further to this embodiment the method comprises administering one or more times a pharmacologically effective amount of one or more other tuberculosis drugs. In this further embodiment the other tuberculosis drugs may be isoniazid, rifampfin, pyrazinamide, or ethambutol. Also in this further embodiment the other tuberculosis drugs may be administered concurrently or consecutively.

In yet another embodiment, the present invention provides a method for treating a pathophysiological condition caused by a bacterium having a malate synthase activity in a subject, comprising administering one or more times a pharmacologically effective amount of the inhibitor described supra to the subject. Further to this embodiment the method comprises administering one or more times a pharmacologically effective amount of one or more other drugs effective to treat the pathophysiological condition. In this further embodiment the pathophysiological condition may be tuberculosis and the other drugs are isoniazid, rifampicin, pyrazinamide, or ethambutol. Also in this further embodiment the other drugs may be administered concurrently or consecutively.

In yet another embodiment of the present invention there is provided a method for designing a potential inhibitory compound of a *Mycobacterium* malate synthase enzyme, comprising identifying a compound in silico that interacts with the malate synthase active site, the identification based at least in part on a computer model of a crystalline structure of the malate synthase enzyme.

Further to this embodiment the method comprises screening the potential compound for inhibition of CoA production by Mycobacterial malate synthase. In this further embodiment the screening steps may comprise contacting a Mycobacterial malate synthase in the presence of an acetate carbon source with the potential compound and measuring production of CoA in the presence and absence of the potential compound; wherein a decrease in a level of CoA production in the presence of the compound compared to a level in the absence of the compound indicates that the potential compound is an inhibitor of the malate synthase. Further still to this further embodiment the method comprises measuring growth inhibition of a *Mycobacteria* culture in the presence of the screened inhibitory compound compared to growth of a control in the absence thereof.

In all embodiments, the potential compound may comprise a carboxylate moiety positioned to contact a Mg2+ ion comprising the malate synthase active site. Also, the potential compound may comprise a ketoacid positioned to bind a Mg2+ ion and a 1,3-diketo moiety positioned to form one or more hydrogen bonds with an amino acid residue functionally equivalent to a Arg-339 residue of native *Mycobacterium tuberculosis* malate synthase, both of the a Mg2+ ion and the functionally equivalent residue comprising the malate synthase active site. Particularly, the functionally equivalent amino acid residue is the native Arg-339 amino acid residue. In addition, the potential compound may comprise a substituted phenyl moiety positioned to overlap an acetyl CoA binding site within the malate synthase. Furthermore, a representative *Mycobacterium* is *Mycobacterium tuberculosis.*

In a related embodiment, the present invention provides an inhibitory compound designed by the screening method as described supra. In another related embodiment the present invention provides a three-dimensional X-ray crystal structure comprising a mycobacterial malate synthase complexed to an inhibitory compound designed by the screening method as described supra.

In yet another embodiment of the present invention there is provided a method for increasing the stability of an aromatic or heteroaromatic diketo acid compound in solution, comprising derivatzing the aromatic ring or the heteroaromatic ring comprising the diketo acid or a prodrug thereof in at least an ortho position with a substituent effective to disrupt coplanarity of the aromatic or heteroaromatic ring with the diketo acid moiety thereby stabilizing the aromatic or heteroaromatic diketo acid compound. In this embodiment aromatic ring is a phenyl or naphthyl moiety and the heteroaromatic ring is a thienyl moiety. Also, in this embodiment the stabilizing substituent may be OH, $NO_2$, $C_{1-6}$alkyl, $C_{1-6}$alkoxy, O($C_{1-6}$alkyl)O($C_{1-6}$alkyl), Br, F, Cl, I, Ph, $PhCH_2$, $PhOCH_3$, $Ph(CH_2)_2$, $CF_3$, $CH_3SO_2$, or imidazolyl. Furthermore, the stabilized aromatic or heteroaromatic diketo acid compound inhibits an activity of a bacterial malate synthase upon contact therewith in vitro or in vivo. A representative bacterium is a *Mycobacterium.*

The well-defined and characterized active site of malate synthase exhibits little conformational change upon substrate binding, thus making it an attractive target for structure-based design. The vital importance of the glyoxlate shunt in persistent bacteria supports the contention that a malate synthase inhibitor could lead to a novel anti-tubercular drug able to control persistent tuberculosis. It is contemplated that the inhibitory compounds and methods provided herein enable a dramatic shortening of TB regimens leading to a better drug therapies and a significant reduction in the outgrowth of drug-resistant TB.

Thus, it is an object of the present invention to provide inhibitors of mycobacterial malate synthase enzyme. Particularly, these compounds are aromatic, heterocyclic, aryl, or heteroaryl substituted diketo acids, for example an analog or derivative of phenyl keto butanoic acid (PKBA). These compounds have the chemical structure:

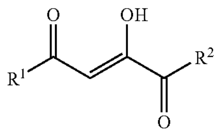

Particularly, $R^1$ may be, but not limited to, aryl groups, such as substituted phenyl groups or a 1- or 2-naphthyl group which may be substituted at one or more of $C_6$-$C_8$. These $R^1$ structures are:

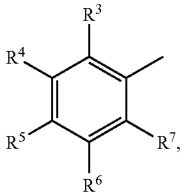

,

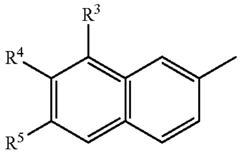

or

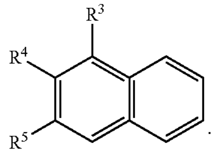

.

The $R^2$ substituent determines if the compound is the diketo acid or the ester, ketone, amide or substituted amide, or aldehyde derivative thereof. For example, $R^2$ may be, although not limited to, a hydrogen, hydroxyl, an alkoxy or the amide or the $C_{1-6}$ alkyl mono- or di-substituted amide. The $R^3$-$R^5$ substituents independently may be a hydrogen, a nitro group, straight or branched-chained alkyl, a halide, an $C_{1-6}$ alkoxy or a $C_{1-6}$ dialkoxy, a phenyl or a substituted phenyl. Although not limited to particular substituents, the alkyl chain may be a $C_{1-5}$ moiety, such as methyl, ethyl, n- or iso-propyl, or a butyl group. The halide may be a fluorine, a bromine, a chlorine, an iodine, or a trifluoromethyl. The phenyl substituent may be substituted with one or two methylenes. The naphthyl substituents may be 1- or 2-naphthyl and may be substituted with $R^3$-$R^5$ at C8, C7 and C6, respectively.

Also, $R^1$ may be a heterocycle or heteroaryl, such as, but not limited to a thiophene, preferably a 2- or 3-thienyl, which may be substituted at C5 with an $R^8$ substituent. These $R^1$ structures may be

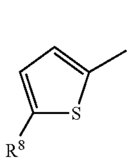

or

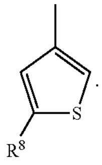

.

The $R^8$ substituents may comprise a phenyl substituted with one or more of $R^3$, $R^4$, $R^5$, $R^6$, $R^7$ substituents or a heterocycle or other heteroaryl moiety, such as, but not limited to, a phenoxyphenyl or methylfuranyl. Other heterocyclic $R^1$ substituents comprise a bithiophenyl, imidazolyl, benzothienyl, furanyl, benzofuranyl, pyridinyl, or pyrrolyl which may be further substituted at available carbons with those substituents as on the phenyl, naphthyl, or thienyl moieties.

Alternatively, these aryl- or heteroaryl-diketo acid compounds may be formulated as a pharmaceutical composition comprising a pharmaceutically acceptable carrier. Such pharmaceutically acceptable carriers are well-known and standard in the art. Without being limiting, such carriers refer to a non-toxic, inert solid, semi-solid liquid filler, diluent, encapsulating material, formulation auxiliary of any type, or simply a sterile aqueous medium, such as saline.

It is a related object to provide a method of chemically stabilizing an aromatic or heteroaromatic diketo acid or a prodrug or close analog of the diketo acid, such as, but not limited to, phenyl keto butanoic acid, naphthyl keto butanoic acid or thienyl keto butanoic acid or carboxylate derivatives thereof. Without being held to theory, it is contemplated that derivatizing the aromatic or heteroaromatic moiety at least at an ortho or equivalent position on the ring perturbs the relative orientation of the ring with the diketoacid moiety thereby disfavoring a retro-Claisen decomposition of the aromatic or heteroaromatic diketo acid. Stabilizing the aromatic or heteroaromatic diketo acid improves inhibitory effects against Mycobacterial or other bacterial cells. Generally, the phenyl keto butanoic acid diketo acid derivatives and analogs provided herein are generally synthesized by condensing the aryl methyl ketone with a suitable dialkyloxalate with subsequent hydrolysis of the formed aryl diketoacid alkyl ester (see Example 2). Prodrugs of the aromatic or heteroaromatic diketo acids may be formed by standard chemical and/or biotechnological methods known in the art.

In addition to potential therapeutic benefits as a drug, inhibitors for malate synthase could be quite effective tools for elucidating and gaining deeper insights in the role this enzyme plays in the various physiological states of the organism. It has been very difficult to study bacteria in the persistent and latent infections because they are composed of bacilli in a dormant non-dividing state. In fact, it is not yet clear what the relationship is between persistent and latent bacilli. It is yet another object of the present invention to validate malate synthase as a drug target for the all stages of tuberculosis infection, i.e., acute, chronic or persistent phase of a *Mycobacterium tuberculosis* (Mtb) infection.

It is a further object of the present invention to use these inhibitors or inhibitory compounds to demonstrate that the inhibition of malate synthase in vivo kills persistent Mtb and has a detrimental effect on all stages of tuberculosis. The effective amount of the malate synthase inhibitor or related-compounds thereof to be used are those amounts effective to produce beneficial results in the recipient subject or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are known and standard in the art.

As is well known in the art, a specific dose level of active compounds such as a malate synthase inhibitor or a related-compound(s) thereof for any particular subject or patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards. One of skill in the art realizes that the effective amount of the malate synthase inhibitor or a related-compound thereof can be the amount that is required to achieve the desired result, that is, although not limited to, reduction/inhibition in production of CoA from acetyl CoA.

Administration of the therapeutic malate synthase inhibitor composition of the present invention to a patient or subject will follow general protocols for the administration of therapies used in treatment of tuberculosis, particularly persistent tuberculosis, taking into account the toxicity, if any, of the malate synthase inhibitor. It is expected that the treatment cycles would be repeated as necessary. It also is contemplated that various standard therapies may be applied in combination, such as concurrent or consecutive co-administration, with the described therapy. Current and standard anti-tubercular drugs include, but are not limited to, isoniazid, rifampicin, pyrazinamide, or ethambutol. It is further contemplated that routes of administration may be those well-known and standard for treatment of tuberculosis. Alternatively, it is well within the ordinary skill of one in this field to determine an effective route of administration of the inhibitory compounds provided herein.

It is contemplated that the inhibitory compounds provided herein are effective to inhibit an activity of malate synthase in a bacterium other than a *Mycobacterium*. The bacteria have a malate synthase enzyme similar to that in *Mycobacteria*, e.g., *Mycobacterium tuberculosis*. It also is contemplated that the inhibitory compounds would therefore be effective therapeutics against pathophysiological conditions associated with these bacteria, particularly associated with a malate synthase activity. As such, a therapeutic regimen for these pathophysiological conditions would also comprise administering one or more times, either concurrently or consecutively, one or more other drugs effective against the pathophysiological condition.

It is contemplated that virtual screens on *M. tuberculosis* malate synthase with a library of commercially available chemicals (2.6 million compounds) may be performed. Compounds identified may be purchased or synthesized by standard chemical synthetic methods and further tested for inhibition against the recombinant malate synthase enzyme as described in the Examples presented herein. Toxicity and therapeutic efficacy of the inhibitory compounds can be determined by standard pharmaceutical procedures in cell or enzyme assays or experimental animals, e.g., for determining the LD50 (the dose lethal to 50% of the population).

Further still it is an object of the present invention to define the three-dimensional X-ray crystal structures of malate synthase bound to inhibitors or potential inhibitory compounds. For the first time, the critical molecular interactions between several structural classes of malate synthase inhibitors are defined. The identification of the key pharmacophoric elements of these chemotypes inherent to inhibition of the enzyme drive structure-based design efforts focused on the optimization of enzyme inhibition, whole cell activity, and physiochemical properties of inhibitors.

The following examples are given for the purpose of illustrating various embodiments of the invention and are not meant to limit the present invention in any fashion.

Example 1

Materials and Methods

Malate Synthase Crystal Structure

Recombinant full-length malate synthase (or GlcB) enzyme is expressed and purified as previously disclosed (1).

Figure 2:
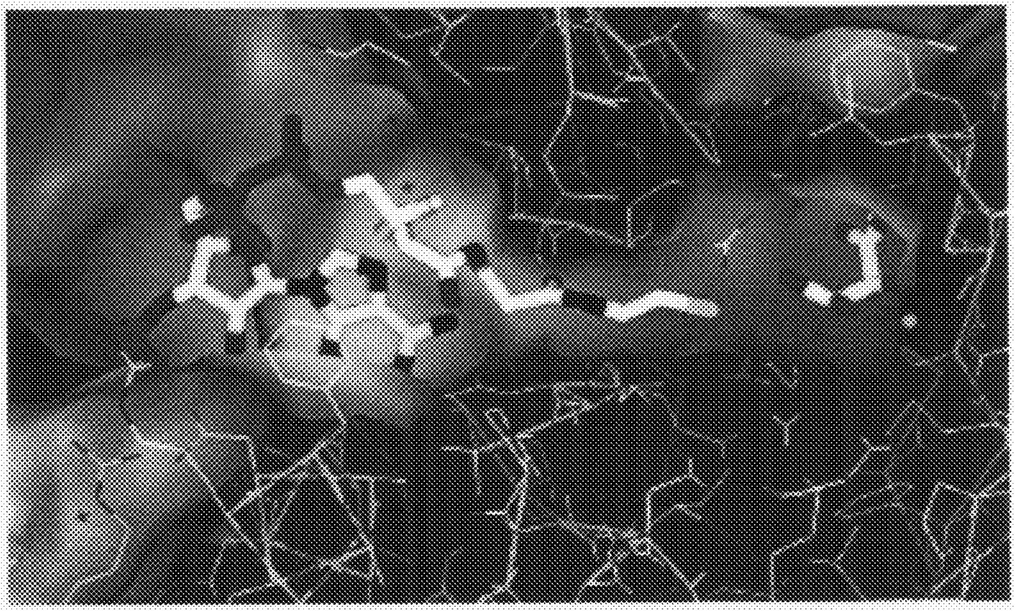
FIG. 2 depicts the active site of malate synthase in complex with CoA and malate.
Figure 3:
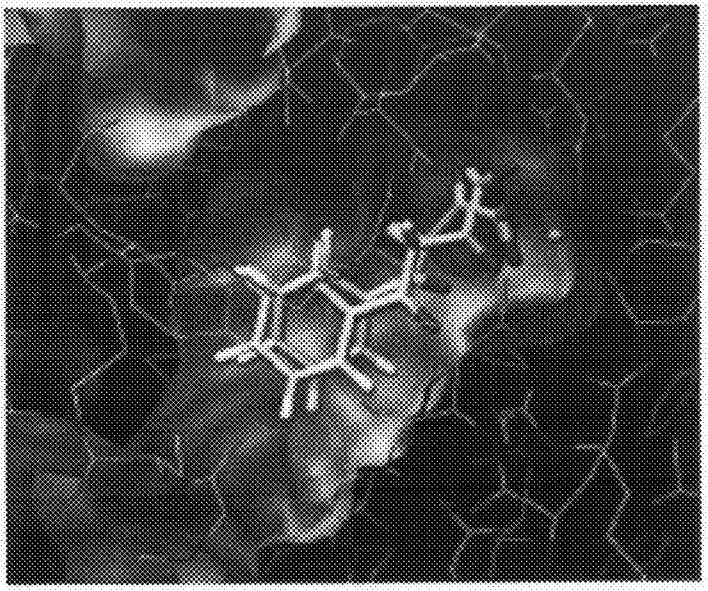
FIG. 3 shows the superposition of docked conformation of 4-phenyl-2,4-diketobutanoic acid (PKBA).
Figure 4:
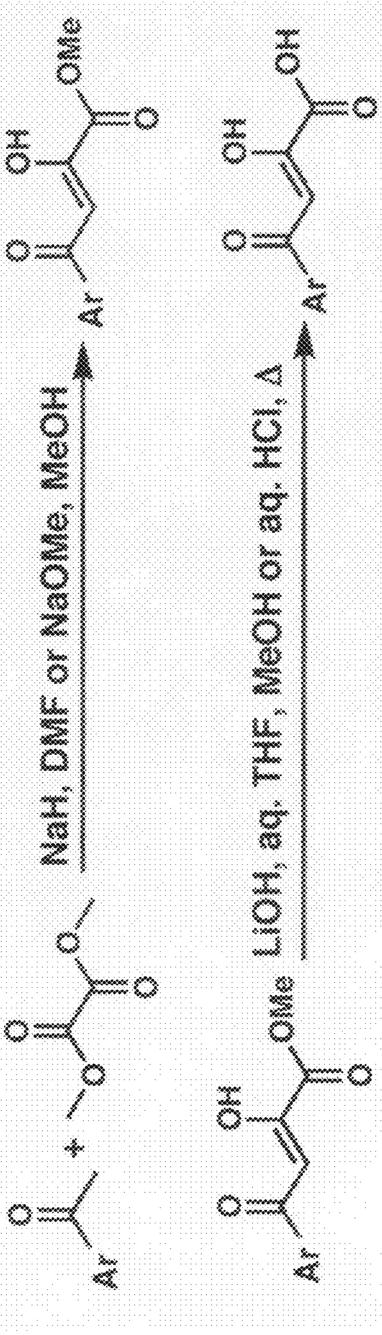
FIG. 4 is the general chemical synthetic scheme for a phenyl-substituted diketo acid.

The structure of malate synthase complexed to the substrate glyoxylate at 2.1 Å resolution and the structure with malate and CoA at 2.7 Å resolution have been described (1). The structure is a TIM barrel fold for the active site-containing domain and a second _-rich domain of unknown function. Unlike ICL, which has an active site on the surface of the protein, malate synthase has a relatively deep and narrow active site (FIG. 2) that extends about 20 Å from the surface of the protein to the bound $Mg^{+2}$ in the bottom of the active site (shown as a blue sphere). This long deep channel binds atoms of the other substrate, CoA.

A co-crystal structure of malate synthase complexed with 4-phenyl-2,4-diketobutanoic acid has also been completed. The inhibitor identified through an initial focused screen has an $IC_{50}$ of 4.0 μM. Crystals of the complex were obtained after preincubation of a 3-fold molar excess of inhibitor with the protein. The structure shows that the carboxylate moiety is in contact with the bound $Mg^{+2}$, similar to the coordination by such groups in glyoxylate and malate, the two keto oxygens face Arg-339 in a coplanar way, and the phenyl group overlaps the CoA binding site, specifically, the hydrophobic part of the channel that binds the pantothenic tail. The diketo-acid functionality resembles a number of inhibitors of HIV-1 integrase (2), which proposedly utilizes carboxy- and carbonyl-oxygens to coordinate two catalytic $Mg^{+2}$ in the active site.

Recombinant Mtb malate synthase with bound inhibitors are produced, purified, and crystallized using full length and truncated forms of the enzyme. The structures and inhibition constants for the full length and truncated enzymes are compared in order to validate the truncated malate synthase for further studies. In addition, 5 other truncated forms of the enzyme are designed in order to try to define the best form of the enzyme to take forward for routine structural studies, i.e. better-diffracting, and inhibition assays.

Truncated Malate Synthase Expression and Purification

A C-terminal truncated form of Mtb malate synthase diffracts to higher resolution than the full length protein. Although it is not yet clear what effect the truncation has on enzyme activity and stability, the crystals appear to be more well-ordered. The truncated gene (encoding residues 1-727) is in the pBH4 plasmid, from Dr. James Remington, University of Oregon. This construct codes for an N-terminal His-tag and a Tobacco-etch virus (TEV) protease cleavage site upstream of the malate synthase sequence.

The purification protocol of truncated malate synthase is very similar to that of the full-length enzyme. The two main differences were that the truncated MLS is expressed at 20 degrees overnight and the His tag is removed by TEV protease cleavage at 4 degrees overnight. The yield is typically about 3.6 mg protein from 1 L culture, equivalent to the full length recombinant protein (FIG. 1).

C619A Mutant

The active site Cys-619, located near the entry portal of the active site access channel, in the wild-type malate synthase enzyme was problematic due to the reactivity of its free thiol sidechain with both oxygen, electrophilic compounds in screening libraries and DTNB. Therefore a C619A mutant, exhibiting >80% of the activity of the wild-type enzyme, was generated. Importantly, inhibitors have nearly identical inhibition constants for wild type and mutant forms of the enzyme, and although the mutant is used in screening, all inhibitors are tested against wild type.

Enzyme Assays

Inhibition of GlcB is measured by an assay that monitors the formation of HSCoA in the forward enzymatic reaction. The assay is conducted in 96- or 384 well plates using 100 or 50 μL overall reaction volumes with 26 nM GlcB being reacted in 20 mM Tris pH 7.5 and 5 mM $MgCl_2$. All inhibitors (in 100% DMSO) were added such that the final reaction mixture contained 1% DMSO. Inhibitors were incubated with GlcB in Tris buffer containing $MgCl_2$ for 20 min at room temperature before adding 0.625 mM acetyl-CoA. The reaction was then initiated by the addition of 1.25 mM glyoxylate. The assay measures the increase in absorbance at 412 nm due to the formation of 5,5'-dithiobis-(2-nitrobenzoic acid) (DTNB)-CoA adduct. DTNB is injected with glyoxylate at the reaction initiation. A BMG LABTECH POLARstar OPTIMA plate reader in absorbance mode was used to continuously monitor the reaction for 20 min per well. Reaction with a 1% DMSO solution instead of inhibitor was taken as the uninhibited control. The percent inhibition was calculated by comparing the slope/min values (representing the enzyme velocity) of an inhibitor trial to the uninhibited control.

A secondary coupled assay with malate dehydrogenase is generated. Malate dehydrogenase uses $NAD^+$ or $NADP^+$ to convert malate to oxaloacetate, and the conversion of NAD or NADPH can be read using either a spectrophotometric assay, or fluoresence. While purified malate dehydrogenase is commercially available from a number of sources (human, porcine, and yeast), of the ones tested the equilibrium of the reaction overwhelmingly favors the production of malate. In order to use malate dehydrogenase in an assay, it is either coupled to another enzyme the can deplete the oxaloacetate or a source of enzyme is found where the reaction favors the production of oxaloacetate.

Whole Cell Assays

Whole-cell activity is assayed using a panel of *M. smegmatis* and *M. tuberculosis* strains, as follows. This assay is based on the fact that growth on either acetate or fatty acids will require ICL1 or ICL2 and malate synthase of the glyoxylate shunt in order for mycobacteria to survive on these carbon sources.

*Mycobacterium smegmatis* $mc^2155$ DglcBDgcl provided by the Dr. John McKinney Lab, is grown on 7H9 media with 0.2% dextrose as it is unable to grow on acetate as a sole carbon source.

*Mycobacterium smegmatis* $mc^2155$ DglcBDgcl, with the *M. smegmatis* glcB deleted, but complemented with *Mycobacterium tuberculosis* glcB, also from the McKinney lab, is grown on M9 media supplemented with 0.5% acetate as the strain can utilize both dextrose and acetate.

*Mycobacterium smegmatis* $mc^24517$ over-expressing *Mycobacterium tuberculosis* glcB on a plasmid, i.e., an "over-expressor" strain is grown on M9+acetate media. Inhibitors of GlcB show a marked reduction of activity. This construct is obtained by incorporation of Mtb malate synthase in an *M. smegmatis* expression vector which is already used as part of the TB Structural Genomics consortium protein production pipeline.

$mc^27000$ *Mycobacterium tuberculosis* vaccine strain with defined RD1 and panC deletions from H37RV (W. R. Jacobs, Albert Einstein College of Medicine, New York, N.Y.) is grown on both 7H9+dextrose and M9+acetate media; GlcB is essential on either carbon source.

*Mycobacterium* wild-type H37Rv is grown on both 7H9+dextrose and 7H9+acetate. It is contemplated that GlcB is essential irrespective of carbon source.

Inhibitors are dissolved in appropriate solvents (typically DMSO-buffer mixtures) and added directly to the cultures over a range of several concentrations. Isoniazid and streptomycin inhibition experiments are run simultaneously to assure quality control. Growth is measured at 24 and 48 hours by taking $OD_{600}$ readings in triplicate. A ten-fold dilution using fresh 7H9 is made when initial optical density readings exceed an absorbance of 1.0. The MIC99 is defined as the concentration of inhibitor that kills 99% of the cultured bacteria.

The level of malate synthase expression in the strain is determined and compared to the standard laboratory strain of *M. smegmatitis* by Western blot analysis. This strain provides a much better read-out of the efficacy of the inhibitors, as it more closely measures the inhibition of the Mtb enzyme. All hits with whole cell activity better than ca. 20 μM are tested against *M. smegmatis* $mc^2$4517. Overexpression of the target gene should lead to resistance to the compound and thus supports the conclusion that the target is malate synthase. Additionally, all hits are examined for inhibition of ICL1 and ICL2, in order determine whether any of the inhibitors have activity against these enzymes as well to determine whether there is overlap in inhibitor activity.

Protocol for the UV-Vis Determination of Stability

A UV-Vis spectrophotometer (Varian Cary 100 Bio) was used for the stability determination. All of the experiments were performed at room temperature using AB buffer as a blank solution which contained 20 mM of Tris-HCl, 5.0 mM of $MgCl_2$ and 0.8 mM of EDTA. The pH of the solution was maintained at 7.5. 100 mM solutions for each compound were prepared in AB buffer and stored at room temperature. A spectrum for each compound was recorded at regular time intervals, e.g. at 0 time, 24 hrs, 2 day, etc. For each compound, the absorption maxima was recorded and an extinction coefficient was calculated using the Beer-Lambert Law. The time required for a 50% reduction (half-life; $t_{1/2}$) for each compound was determined.

Example 2

Phenyl Keto Butanoic Acid (PKBA) Inhibits GlcB

Figure 5:
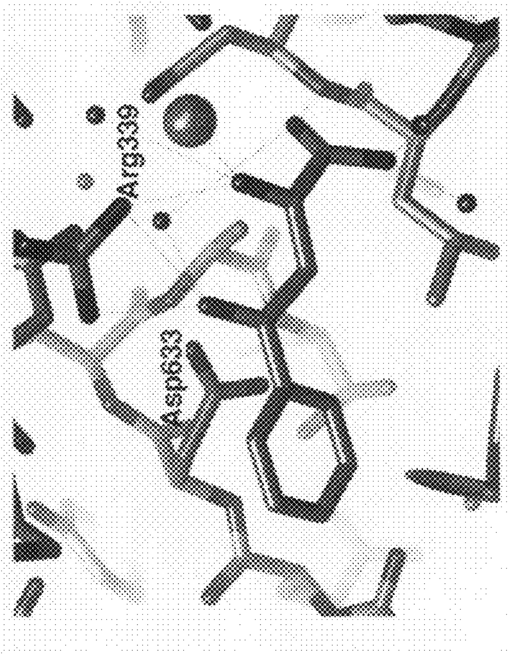
FIG. 5 is a high-resolution crystal structure of wild-type GlcB depicting phenyl keto butanoic acid contacts with the GlcB active site.

A high resolution (1.8 Å) crystal structure of wild-type GlcB:PKBA (FIG. 5) demonstrated bidentate binding of the ketoacid moiety to the active-site $Mg^{+2}$, hydrogen-bonding of the ketoacid ketone oxygen and the aryl ketone oxygen to Arg-339, and hydrophobic interactions of the phenyl substituent with Leu-461, Met-515, Thr-517, Cys-619, and Met-631. Thus, PKBA derivatives and analogs optimizing the aromatic moiety and the diketo acid framework are synthesized.

Chemical Synthesis of Phenyl Keto Butanoic Acid (PKBA) Derivatives and Analogs

The synthesis of PKBA (FIG. 5) and its analogs has relied on the initial Claisen condensation of the appropriate aryl/heteroaryl methyl ketone with a suitable dialkyloxalate in the presence of a base, typically a metal alkoxide or hydride, in a polar solvent such as dimethylformamide or an alcohol to afford the PKBA alkyl ester. The alkyl ester may be hydrolyzed to afford the corresponding diketoacid with a strong acid or base. It should be noted that more highly functionalized aryl/heteroaryl-substituted methyl ketones were prepared through Suzuki-Miyaura coupling of the appropriate boronic acid/ester with a suitable aryl/heteroaryl halide.

In general, all reactions were conducted in the air without any precautions taken for excluding oxygen and/or moisture, unless noted otherwise. Silica gel chromatography was performed with an Isco Companion 4×, utilizing a hexane/ethyl acetate gradient and an appropriately sized gel cartridge. Unless noted otherwise, compounds >95% pure by $^1H$ NMR and LC-MS analysis. LC-MS analyses were performed utilizing an Shimadzu 2010-EV instrument. NMR spectra were recorded on a Bruker 400 MHz spectrometer. The chemical shifts (δ) for $^1H$ spectra are reported in ppm relative to residual signals of the solvent.

The ortho-alkylacetophenones, where the alkyl group is ethyl, n-propyl, and i-propyl, were prepared via the method of Cahiez et al (Org. Lett. 2004, 6, 4395-4398) and then utilized with the below pertinent procedure to prepare the corresponding aryldiketo methyl ester and acid.

Sample Protocol for Suzuki-Miyaura Couplings—Preparation of 1-(5-(4-hydroxyphenyl)thiophen-2-yl)ethanone A flame-dried test tube under $N_2$ was charged with 1-(5-bromothiophen-2-yl)ethanone (250 mg, 1.22 mmol), p-hydroxyphenylboronic acid (1.2 equiv, 1.40 mmol, 202 mg), and 2.0 mL 1,4-dioxane. To the yellow solution, tetrakistriphenylphosphinepalladium(0) (6 mol %, 0.0731 mmol, 84 mg) and 2 M aqueous sodium carbonate (2.0 equiv, 2.44 mmol, 2.0 mL) were added. The yellow mixture was heated to 100° C. for 18 h. The resulting yellow-brown mixture was cooled to rt, adsorbed onto Celite in vacuo, and purified by silica gel chromatography to afford the desired product as an analytically pure yellow solid (51 mg, 19% yield).

Sample protocol for Claisen Condensations—Preparation of (Z)-methyl 4-(2-chloro-6-fluoro-3-methylphenyl)-2-hydroxy-4-oxobut-2-enoate:

2'-chloro-6'-fluoro-3'-methylacetophenone (1.00 g, 5.36 mmol) was dissolved in 2.0 mL anhydrous methanol under $N_2$ and subjected to the addition of 25% sodium methoxide in methanol (2.2 equiv, 11.8 mmol, 2.7 mL) via syringe. The nearly colorless solution was stirred for 30 min and then dimethyl oxalate (2.2 equiv, 11.8 mmol, 1.39 g) was added. The cloudy white mixture was stirred at 30° C. After 15 h, the cloudy white mixture was quenched with 2.0 mL 2 M $HCl_{(aq)}$ and extracted with 3×10 mL EtOAc. The light yellow organics were washed with 10 mL saturated brine solution, dried over anhydrous $MgSO_4$ for 5 min, filtered, and concentrated in vacuo to afford a light yellow solid. Silica gel chromatography followed by recrystallization from hot hexanes/dichloromethane (ca. 5:1) afforded the desired product as analytically pure white needles (688 mg, 47% yield).

Sample protocol for Methyl Ester Hydrolyses—Preparation of (Z)-2-hydroxy-4-(2-methyl-5-phenylthiophen-3-yl)-4-oxobut-2-enoic acid:

(Z)-methyl 2-hydroxy-4-(2-methyl-5-phenylthiophen-3-yl)-4-oxobut-2-enoate (32 mg, 0.106 mmol) was dissolved in 2 mL of 2:1:1 ($THF/CH_3OH/H_2O$) and subjected to the addition of LiOH monohydrate (2.0 equiv, 0.212 mmol, 9 mg). The yellow solution was stirred for 7 h and then extracted with 3×6 mL $Et_2O$. The aqueous phase was acidified to ca. pH 1 with 2 M $HCl_{(aq)}$ and the resulting cloudy mixture was extracted with 2×5 mL EtOAc. The light yellow organics were dried over anhydrous $MgSO_4$ for 5 min, filtered, and concentrated in vacuo to afford the desired product as an analytically pure yellow solid (21 mg, 68% yield).

Example 3

Synthesized Compounds and NMR Data

(Z)-4-(2,5-difluorophenyl)-2-hydroxy-4-oxobut-2-enoic acid $^1H$ NMR ($d_1$-chloroform) δ 7.62 (d, 1, Ar), 7.57 (d, 1, Ar), 7.53 (s, 1, Ar), 6.91 (s, 1, CH).

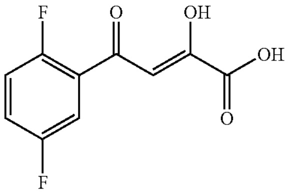 [SMILES: O=C(O)/C(O)=C/C(=O)c1cc(F)ccc1F]

(Z)-4-(2-fluoro-5-methoxyphenyl)-2-hydroxy-4-oxobut-2-enoic acid $^{1}$H NMR ($d_1$-chloroform) δ 7.51 (s, 1, Ar), 7.45 (d, 1, Ar), 7.39 (d, 1, Ar), 6.80 (s, 1, CH), 3.96 (s, 3, $CH_3$).

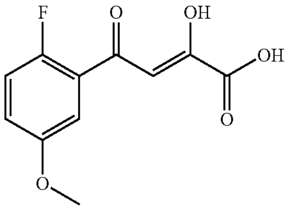 [SMILES: COc1ccc(F)c(C(=O)/C=C(\O)C(=O)O)c1]

(Z)-4-(2-fluoro-4-methoxyphenyl)-2-hydroxy-4-oxobut-2-enoic acid $^{1}$H NMR ($d_1$-chloroform) δ 7.51 (s, 1, Ar), 7.45 (d, 1, Ar), 7.41 (d, 1, Ar), 6.89 (s, 1, CH), 3.97 (s, 3, $CH_3$).

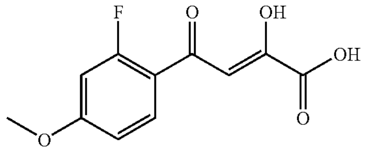 [SMILES: COc1ccc(C(=O)/C=C(\O)C(=O)O)c(F)c1]

(Z)-4-(2,6-dichlorophenyl)-2-hydroxy-4-oxobut-2-enoic acid $^{1}$H NMR ($d_1$-chloroform) δ 7.93 (t, 1, Ar), 7.52 (d, 2, Ar), 6.95 (s, 1, CH).

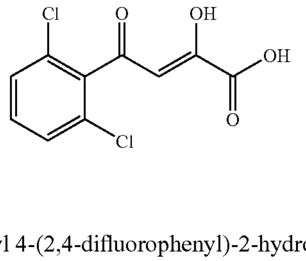

(Z)-methyl 4-(2,4-difluorophenyl)-2-hydroxy-4-oxobut-2-enoate $^{1}$H NMR ($d_1$-chloroform) δ 7.78 (d, 1, Ar), 7.62 (d, 1, Ar), 7.41 (s, 1, Ar), 7.02 (s, 1, CH), 3.82 (s, 3, $CH_3$).

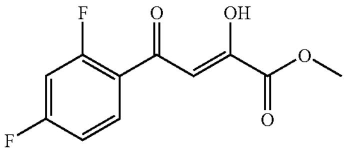 [SMILES: COC(=O)/C(O)=C/C(=O)c1ccc(F)cc1F]

(Z)-4-(2,4-difluorophenyl)-2-hydroxy-4-oxobut-2-enoic acid $^{1}$H NMR ($d_1$-chloroform) δ 7.81 (d, 1, Ar), 7.66 (d, 1, Ar), 7.45 (s, 1, Ar), 7.10 (s, 1, CH).

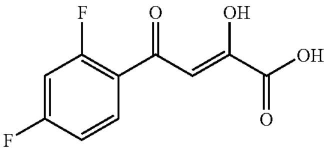 [SMILES: O=C(O)/C(O)=C/C(=O)c1ccc(F)cc1F]

(Z)-methyl 4-(2,5-dichlorophenyl)-2-hydroxy-4-oxobut-2-enoate $^{1}$H NMR ($d_1$-chloroform) δ 8.01 (d, 1, Ar), 7.77 (s, 1, Ar), 7.65 (d, 1, Ar), 6.99 (s, 1, CH), 3.78 (s, 3, $CH_3$).

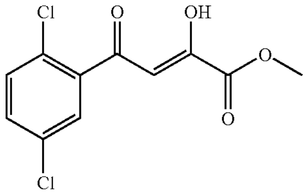 [SMILES: COC(=O)/C(O)=C/C(=O)c1cc(Cl)ccc1Cl]

(Z)-4-(2,5-dichlorophenyl)-2-hydroxy-4-oxobut-2-enoic acid $^{1}$H NMR ($d_1$-chloroform) δ 8.08 (d, 1, Ar), 7.79 (s, 1, Ar), 7.70 (d, 1, Ar), 7.02 (s, 1, CH)

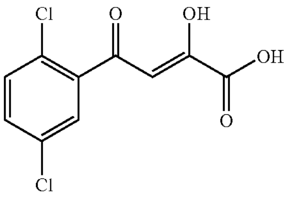 [SMILES: O=C(O)/C(O)=C/C(=O)c1cc(Cl)ccc1Cl]

(Z)-methyl 4-(3,5-difluorophenyl)-2-hydroxy-4-oxobut-2-enoate $^{1}$H NMR ($d_1$-chloroform) δ 7.32 (s, 2, Ar), 7.19 (d, 1, Ar), 6.99 (s, 1, CH), 3.81 (s, 3, $CH_3$).

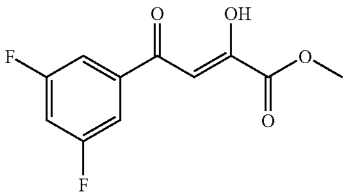 [SMILES: COC(=O)/C(O)=C/C(=O)c1cc(F)cc(F)c1]

(Z)-4-(3,5-difluorophenyl)-2-hydroxy-4-oxobut-2-enoic acid $^1$H NMR ($d_1$-chloroform) δ 7.32 (s, 2, Ar), 7.19 (d, 1, Ar), 6.99 (s, 1, CH).

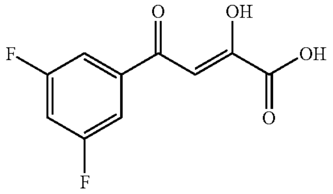 [SMILES: O=C(O)/C(O)=C/C(=O)c1cc(F)cc(F)c1]

(Z)-methyl 4-(2,4-dichlorophenyl)-2-hydroxy-4-oxobut-2-enoate $^1$H NMR ($d_1$-chloroform) δ 7.78 (d, 1, Ar), 7.72 (s, 1, Ar), 7.60 (d, 1, Ar), 7.02 (s, 1, CH), 3.88 (s, 3, $CH_3$).

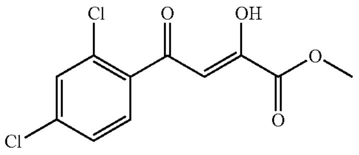 [SMILES: COC(=O)/C(O)=C/C(=O)c1ccc(Cl)cc1Cl]

(Z)-4-(2,4-dichlorophenyl)-2-hydroxy-4-oxobut-2-enoic acid $^1$H NMR ($d_1$-chloroform) δ 7.80 (d, 1, Ar), 7.74 (s, 1, Ar), 7.62 (d, 1, Ar), 7.05 (s, 1, CH).

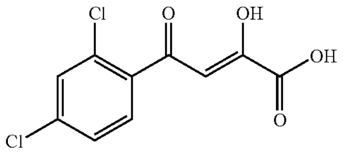 [SMILES: O=C(O)/C(O)=C/C(=O)c1ccc(Cl)cc1Cl]

(Z)-methyl 4-(2,6-difluorophenyl)-2-hydroxy-4-oxobut-2-enoate $^1$H NMR ($d_1$-chloroform) δ 7.60 (t, 1, Ar), 7.25 (d, 2, Ar), 6.97 (s, 1, CH), 3.91 (s, 3, $CH_3$).

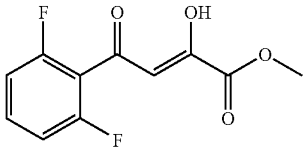 [SMILES: COC(=O)/C(O)=C/C(=O)c1c(F)cccc1F]

(Z)-4-(2,6-difluorophenyl)-2-hydroxy-4-oxobut-2-enoic acid $^1$H NMR ($d_1$-chloroform) δ 7.61 (t, 1, Ar), 7.27 (d, 2, Ar), 6.99 (s, 1, CH).

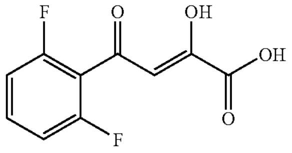 [SMILES: O=C(O)/C(O)=C/C(=O)c1c(F)cccc1F]

(Z)-methyl 2-hydroxy-4-oxo-4-(perfluorophenyl)but-2-enoate $^1$H NMR ($d_1$-chloroform) δ 6.96 (s, 1, CH), 3.95 (s, 3, $CH_3$).

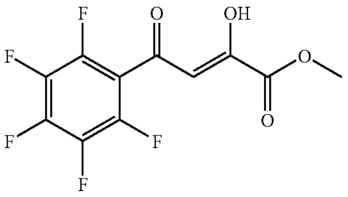 [SMILES: COC(=O)/C(O)=C/C(=O)c1c(F)c(F)c(F)c(F)c1F]

(Z)-2-hydroxy-4-oxo-4-(perfluorophenyl)but-2-enoic acid $^1$H NMR ($d_1$-chloroform) δ 6.96 (s, 1, CH).

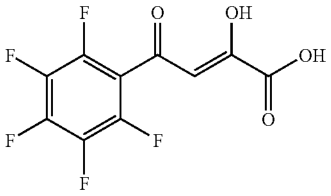 [SMILES: O=C(O)/C(O)=C/C(=O)c1c(F)c(F)c(F)c(F)c1F]

(Z)-methyl 2-hydroxy-4-oxo-4-(2,4,5-trifluorophenyl)but-2-enoate $^1$H NMR ($d_1$-chloroform) δ 7.72 (s, 1, Ar), 7.52 (s, 1, Ar), 6.98 (s, 1, CH), 3.92 (s, 3, $CH_3$).

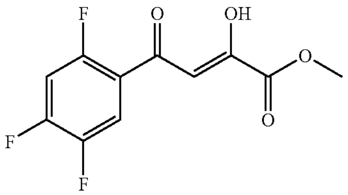 [SMILES: COC(=O)/C(O)=C/C(=O)c1cc(F)c(F)cc1F]

(Z)-2-hydroxy-4-oxo-4-(2,4,5-trifluorophenyl)but-2-enoic acid $^{1}H$ NMR ($d_1$-chloroform) δ 7.74 (s, 1, Ar), 7.55 (s, 1, Ar), 7.01 (s, 1, CH).

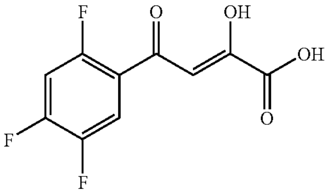 [SMILES: O=C(O)/C(O)=C/C(=O)c1cc(F)c(F)cc1F]

(Z)-methyl 4-(2-bromo-4-chlorophenyl)-2-hydroxy-4-oxobut-2-enoate $^{1}H$ NMR ($d_1$-chloroform) δ 8.05 (s, 1, Ar), 7.71 (d, 1, Ar), 7.62 (d, 1, Ar), 7.01 (s, 1, CH), 3.95 (s, 3, $CH_3$).

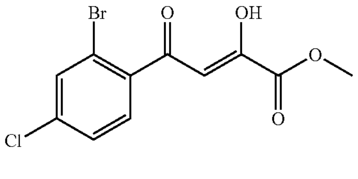 [SMILES: COC(=O)/C(O)=C/C(=O)c1ccc(Cl)cc1Br]

(Z)-4-(2-bromo-4-chlorophenyl)-2-hydroxy-4-oxobut-2-enoic acid $^{1}H$ NMR ($d_1$-chloroform) δ 8.08 (s, 1, Ar), 7.73 (d, 1, Ar), 7.65 (d, 1, Ar), 7.05 (s, 1, CH).

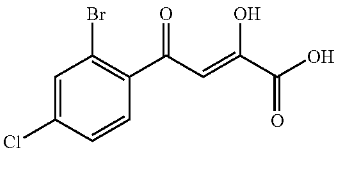 [SMILES: O=C(O)/C(O)=C/C(=O)c1ccc(Cl)cc1Br]

(Z)-4-(3,5-dibromo-4-hydroxyphenyl)-2-hydroxy-4-oxobut-2-enoic acid $^{1}H$ NMR ($d_1$-chloroform) δ 7.95 (s, 2, Ar), 7.06 (s, 1, CH), 5.45 (s, 1, phenolic OH).

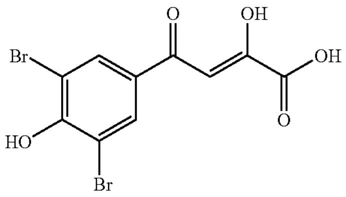 [SMILES: O=C(O)/C(O)=C/C(=O)c1cc(Br)c(O)c(Br)c1]

(Z)-methyl 4-(2-bromo-4-fluorophenyl)-2-hydroxy-4-oxobut-2-enoate $^{1}H$ NMR ($d_1$-chloroform) δ 7.78 (d, 1, Ar), 7.69 (s, 1, Ar), 7.56 (d, 1, Ar), 6.95 (s, 1, CH), 3.98 (s, 3, $CH_3$).

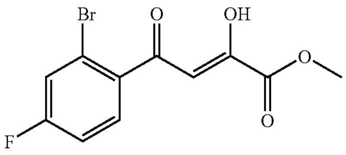

(Z)-4-(2-bromo-4-fluorophenyl)-2-hydroxy-4-oxobut-2-enoic acid $^{1}H$ NMR ($d_1$-chloroform) δ 7.79 (d, 1, Ar), 7.71 (s, 1, Ar), 7.58 (d, 1, Ar), 6.99 (s, 1, CH).

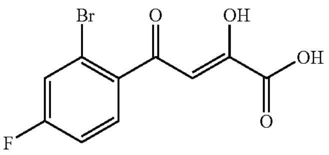 [SMILES: O=C(O)/C(O)=C/C(=O)c1ccc(F)cc1Br]

(Z)-methyl 2-hydroxy-4-oxo-4-(2,4,6-trifluorophenyl)but-2-enoate $^{1}H$ NMR ($d_1$-chloroform) δ 7.69 (s, 2, Ar), 6.99 (s, 1, CH), 3.99 (s, 3, $CH_3$).

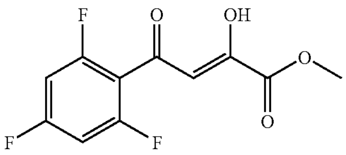

(Z)-2-hydroxy-4-oxo-4-(2,4,6-trifluorophenyl)but-2-enoic acid $^{1}H$ NMR ($d_1$-chloroform) δ 7.70 (s, 2, Ar), 7.01 (s, 1, CH).

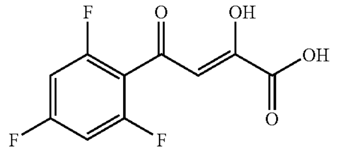 [SMILES: O=C(O)/C(O)=C/C(=O)c1c(F)cc(F)cc1F]

(Z)-methyl 4-([2,2'-bithiophen]-5-yl)-2-hydroxy-4-oxobut-2-enoate $^1$H NMR ($d_1$-chloroform) δ 8.01 (d, 1, Ar), 7.83 (d, 1, Ar), 7.75 (d, 1, Ar), 7.70 (d, 1, Ar), 7.45 (t, 1, Ar), 7.09 (s, 1, CH), 3.99 (s, 3, $CH_3$).

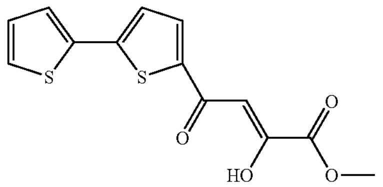 [SMILES: COC(=O)/C(O)=C/C(=O)c1ccc(-c2cccs2)s1]

(Z)-4-([2,2'-bithiophen]-5-yl)-2-hydroxy-4-oxobut-2-enoic acid $^1$H NMR ($d_1$-chloroform) δ 8.05 (d, 1, Ar), 7.87 (d, 1, Ar), 7.78 (d, 1, Ar), 7.73 (d, 1, Ar), 7.48 (t, 1, Ar), 7.10 (s, 1, CH).

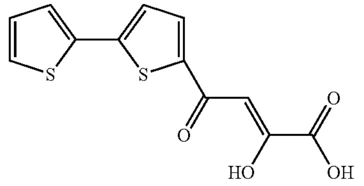 [SMILES: O=C(O)/C(O)=C/C(=O)c1ccc(-c2cccs2)s1]

(Z)-methyl 2-hydroxy-4-(4-(methylsulfonyl)phenyl)-4-oxobut-2-enoate $^1$H NMR ($d_1$-chloroform) δ 8.21 (d, 2, Ar), 8.12 (d, 2, Ar), 7.01 (s, 1, CH), 3.98 (s, 3, $CH_3$), 3.29 (s, 3, $CH_3$).

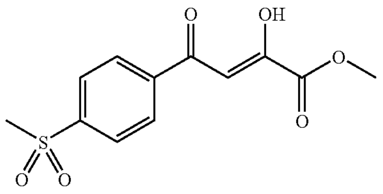

(Z)-2-hydroxy-4-(4-(methylsulfonyl)phenyl)-4-oxobut-2-enoic acid $^1$H NMR ($d_1$-chloroform) δ 8.21 (d, 2, Ar), 8.12 (d, 2, Ar), 7.01 (s, 1, CH), 3.29 (s, 3, $CH_3$).

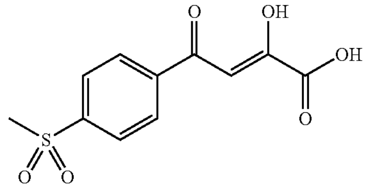 [SMILES: CS(=O)(=O)c1ccc(C(=O)/C=C(\O)C(=O)O)cc1]

(Z)-methyl 4-(4-(1H-imidazol-1-yl)phenyl)-2-hydroxy-4-oxobut-2-enoate $^1$H NMR ($d_1$-chloroform) δ 7.92 (d, 2, Ar), 7.84 (d, 2, Ar), 7.52 (d, 1, Ar), 7.21 (d, 1, Ar), 7.20 (s, 1, Ar), 7.01 (s, 1, CH), 3.98 (s, 3, $CH_3$).

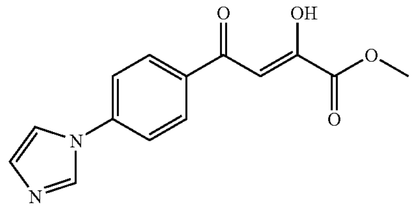 [SMILES: COC(=O)/C(O)=C/C(=O)c1ccc(-n2ccnc2)cc1]

(Z)-4-(4-(1H-imidazol-1-yl)phenyl)-2-hydroxy-4-oxobut-2-enoic acid $^1$H NMR ($d_1$-chloroform) δ 7.93 (d, 2, Ar), 7.86 (d, 2, Ar), 7.53 (d, 1, Ar), 7.24 (d, 1, Ar), 7.21 (s, 1, Ar), 7.01 (s, 1, CH).

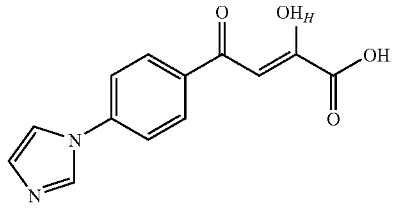

(Z)-methyl 4-(4-(2,5-dioxo-2,5-dihydro-1H-pyrrol-1-yl)phenyl)-2-hydroxy-4-oxobut-2-enoate $^1$H NMR ($d_1$-chloroform) δ 7.95 (d, 2, Ar), 7.77 (d, 2, Ar), 7.01 (s, 1, CH), 6.92 (d, 2, CH), 3.98 (s, 3, $CH_3$).

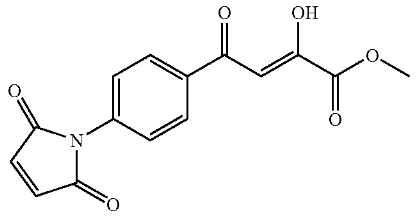 [SMILES: COC(=O)/C(O)=C/C(=O)c1ccc(N2C(=O)C=CC2=O)cc1]

(Z)-4-(4-(2,5-dioxo-2,5-dihydro-1H-pyrrol-1-yl)phenyl)-2-hydroxy-4-oxobut-2-enoic acid $^1$H NMR ($d_1$-chloroform) δ 7.97 (d, 2, Ar), 7.79 (d, 2, Ar), 7.04 (s, 1, CH), 6.96 (d, 2, CH).

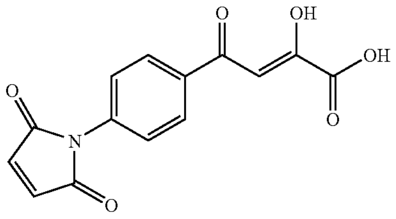 [SMILES: O=C(O)/C(O)=C/C(=O)c1ccc(N2C(=O)C=CC2=O)cc1]

(Z)-methyl 4-(6-chloro-2-fluoro-3-methylphenyl)-2-hydroxy-4-oxobut-2-enoate $^1$H NMR ($d_1$-chloroform) δ 7.52 (d, 1, Ar), 7.35 (d, 1, Ar), 6.99 (s, 1, CH), 3.98 (s, 3, $CH_3$), 2.41 (s, 3, $CH_3$).

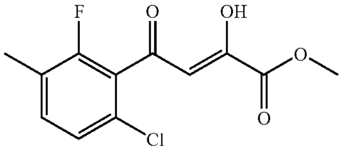

(Z)-4-(6-chloro-2-fluoro-3-methylphenyl)-2-hydroxy-4-oxobut-2-enoic acid $^1$H NMR ($d_1$-chloroform) δ 7.53 (d, 1, Ar), 7.37 (d, 1, Ar), 7.01 (s, 1, CH), 2.41 (s, 3, $CH_3$).

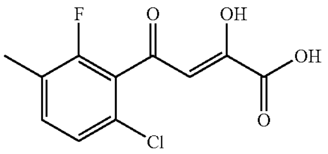 [SMILES: Cc1ccc(Cl)c(C(=O)/C=C(\O)C(=O)O)c1F]

(Z)-2-hydroxy-4-(3-methyl-5-phenylthiophen-2-yl)-4-oxobut-2-enoic acid $^1$H NMR ($d_1$-chloroform) δ 7.81 (d, 2, Ar), 7.53 (t, 2, Ar), 7.42 (t, 1, Ar), 7.15 (s, 1, Ar), 7.01 (s, 1, CH), 2.44 (s, 3, $CH_3$).

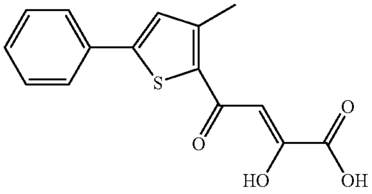 [SMILES: Cc1cc(-c2ccccc2)sc1C(=O)/C=C(\O)C(=O)O]

(Z)-methyl 2-hydroxy-4-(3-methyl-5-phenylthiophen-2-yl)-4-oxobut-2-enoate $^1$H NMR ($d_1$-chloroform) δ 7.81 (d, 2, Ar), 7.53 (t, 2, Ar), 7.42 (t, 1, Ar), 7.15 (s, 1, Ar), 7.01 (s, 1, CH), 3.98 (s, 3, $CH_3$), 2.44 (s, 3, $CH_3$).

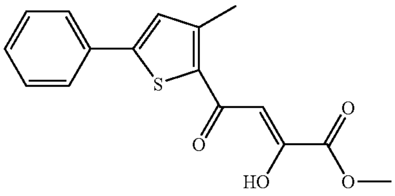 [SMILES: COC(=O)/C(O)=C/C(=O)c1sc(-c2ccccc2)cc1C]

(Z)-methyl 2-hydroxy-4-(5-(4-methoxyphenyl)thiophen-2-yl)-4-oxobut-2-enoate $^1$H NMR ($d_1$-chloroform) δ 8.01 (d, 1, Ar), 7.99 (d, 1, Ar), 7.69 (d, 2, Ar), 7.15 (d, 2, Ar), 6.99 (s, 1, CH), 3.99 (s, 3, $CH_3$), 3.86 (s, 3, $CH_3$).

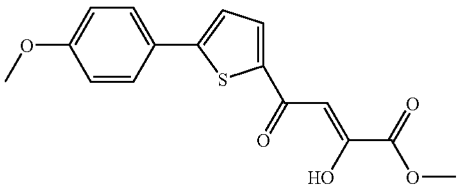

(Z)-2-hydroxy-4-(5-(4-methoxyphenyl)thiophen-2-yl)-4-oxobut-2-enoic acid $^1$H NMR ($d_1$-chloroform) δ 8.02 (d, 1, Ar), 8.0 (d, 1, Ar), 7.71 (d, 2, Ar), 7.20 (d, 2, Ar), 7.01 (s, 1, CH), 3.88 (s, 3, $CH_3$).

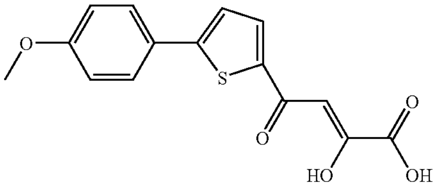 [SMILES: COc1ccc(-c2ccc(C(=O)/C=C(\O)C(=O)O)s2)cc1]

(Z)-methyl 4-(5-(4-fluorophenyl)thiophen-2-yl)-2-hydroxy-4-oxobut-2-enoate $^1$H NMR ($d_1$-chloroform) δ 8.00 (d, 1, Ar), 7.99 (d, 1, Ar), 7.68 (d, 2, Ar), 7.25 (d, 2, Ar), 6.99 (s, 1, CH), 3.99 (s, 3, $CH_3$).

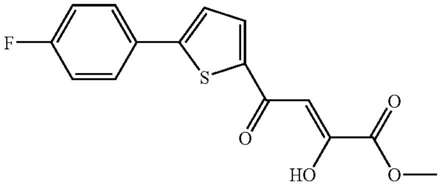 [SMILES: COC(=O)/C(O)=C/C(=O)c1ccc(-c2ccc(F)cc2)s1]

(Z)-4-(5-(4-fluorophenyl)thiophen-2-yl)-2-hydroxy-4-oxobut-2-enoic acid $^1$H NMR ($d_1$-chloroform) δ 8.01 (d, 1, Ar), 8.00 (d, 1, Ar), 7.69 (d, 2, Ar), 7.26 (d, 2, Ar), 6.99 (s, 1, CH).

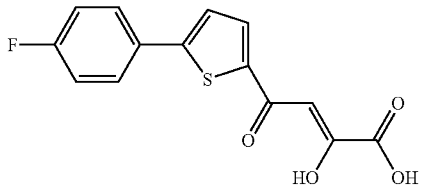 [SMILES: O=C(O)/C(O)=C/C(=O)c1ccc(-c2ccc(F)cc2)s1]

(Z)-methyl 2-hydroxy-4-oxo-4-(5-(4-(trifluoromethyl)phenyl)thiophen-2-yl)but-2-enoate $^1$H NMR ($d_1$-chloroform) δ 8.02 (d, 1, Ar), 8.01 (d, 1, Ar), 7.70 (d, 2, Ar), 7.68 (d, 2, Ar), 6.98 (s, 1, CH), 3.97 (s, 3, $CH_3$).

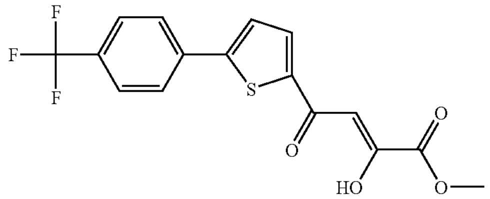 [SMILES: COC(=O)/C(O)=C/C(=O)c1ccc(-c2ccc(C(F)(F)F)cc2)s1]

(Z)-2-hydroxy-4-oxo-4-(5-(4-(trifluoromethyl)phenyl)thiophen-2-yl)but-2-enoic acid $^1$H NMR ($d_1$-chloroform) δ 8.01 (d, 1, Ar), 8.00 (d, 1, Ar), 7.71 (d, 2, Ar), 7.69 (d, 2, Ar), 6.99 (s, 1, CH).

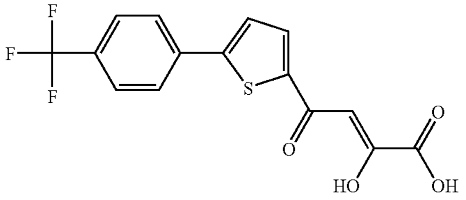 [SMILES: O=C(O)/C(O)=C/C(=O)c1ccc(-c2ccc(C(F)(F)F)cc2)s1]

(Z)-methyl 2-hydroxy-4-(5-(4-hydroxyphenyl)thiophen-2-yl)-4-oxobut-2-enoate $^1$H NMR ($d_1$-chloroform) δ 7.99 (d, 1, Ar), 7.98 (d, 1, Ar), 7.69 (d, 2, Ar), 7.59 (d, 2, Ar), 6.99 (s, 1, CH), 5.41 (s, 1, OH), 3.99 (s, 3, $CH_3$).

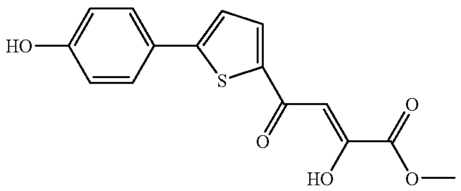 [SMILES: COC(=O)/C(O)=C/C(=O)c1ccc(-c2ccc(O)cc2)s1]

(Z)-2-hydroxy-4-(5-(4-hydroxyphenyl)thiophen-2-yl)-4-oxobut-2-enoic acid $^1$H NMR ($d_1$-chloroform) δ 8.00 (d, 1, Ar), 7.99 (d, 1, Ar), 7.70 (d, 2, Ar), 7.62 (d, 2, Ar), 6.98 (s, 1, CH).

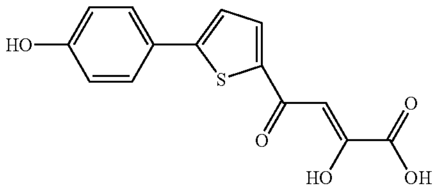 [SMILES: O=C(O)/C(O)=C/C(=O)c1ccc(-c2ccc(O)cc2)s1]

(Z)-methyl 4-(benzo[b]thiophen-2-yl)-2-hydroxy-4-oxobut-2-enoate $^1$H NMR ($d_1$-chloroform) δ 8.31 (s, 1, Ar), 7.99 (d, 1, Ar), 7.79 (d, 1, Ar), 7.55 (t, 1, Ar), 7.51 (t, 1, Ar), 7.00 (s, 1, CH), 3.98 (s, 3, $CH_3$).

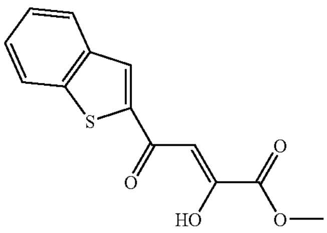 [SMILES: COC(=O)/C(O)=C/C(=O)c1cc2ccccc2s1]

(Z)-4-(benzo[b]thiophen-2-yl)-2-hydroxy-4-oxobut-2-enoic acid $^1$H NMR ($d_1$-chloroform) δ 8.34 (s, 1, Ar), 8.01 (d, 1, Ar), 7.81 (d, 1, Ar), 7.58 (t, 1, Ar), 7.54 (t, 1, Ar), 7.01 (s, 1, CH).

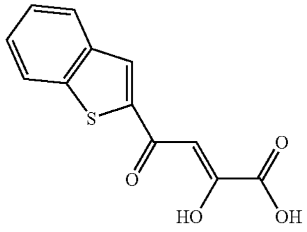 [SMILES: O=C(O)/C(O)=C/C(=O)c1cc2ccccc2s1]

(Z)-methyl 4-(5-(4-chlorophenyl)thiophen-2-yl)-2-hydroxy-4-oxobut-2-enoate $^1$H NMR ($d_1$-chloroform) δ 8.04 (d, 1, Ar), 8.03 (d, 1, Ar), 7.75 (d, 2, Ar), 7.55 (d, 2, Ar), 6.98 (s, 1, CH), 3.98 (s, 3, $CH_3$).

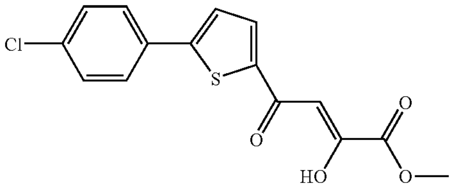 [SMILES: COC(=O)/C(O)=C/C(=O)c1ccc(-c2ccc(Cl)cc2)s1]

(Z)-4-(5-(4-chlorophenyl)thiophen-2-yl)-2-hydroxy-4-oxobut-2-enoic acid $^1$H NMR ($d_1$-chloroform) δ 8.02 (d, 1, Ar), 8.01 (d, 1, Ar), 7.76 (d, 2, Ar), 7.54 (d, 2, Ar), 6.99 (s, 1, CH).

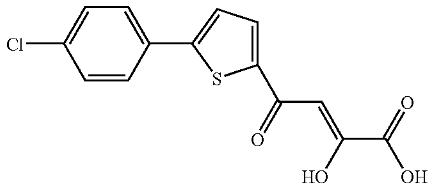 [SMILES: O=C(O)/C(O)=C/C(=O)c1ccc(-c2ccc(Cl)cc2)s1]

(Z)-methyl 2-hydroxy-4-oxo-4-(5-(4-phenoxyphenyl)thiophen-2-yl)but-2-enoate $^{1}$H NMR ($d_1$-chloroform) δ 8.00 (d, 1, Ar), 7.99 (d, 1, Ar), 7.75 (d, 2, Ar), 7.45 (t, 2, Ar), 7.25 (d, 2, Ar), 7.20 (t, 1, Ar), 7.12 (d, 2, Ar), 6.88 (s, 1, CH), 3.98 (s, 3, $CH_3$).

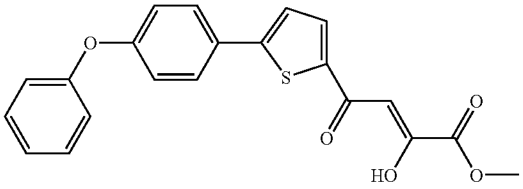 [SMILES: COC(=O)/C(O)=C/C(=O)c1ccc(-c2ccc(Oc3ccccc3)cc2)s1]

(Z)-2-hydroxy-4-oxo-4-(5-(4-phenoxyphenyl)thiophen-2-yl)but-2-enoic acid $^{1}$H NMR ($d_1$-chloroform) δ 8.01 (d, 1, Ar), 8.00 (d, 1, Ar), 7.76 (d, 2, Ar), 7.46 (t, 2, Ar), 7.24 (d, 2, Ar), 7.21 (t, 1, Ar), 7.13 (d, 2, Ar), 6.90 (s, 1, CH)

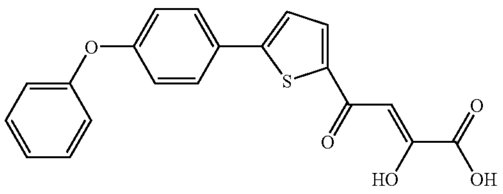 [SMILES: O=C(O)/C(O)=C/C(=O)c1ccc(-c2ccc(Oc3ccccc3)cc2)s1]

(Z)-methyl 2-hydroxy-4-(5-methylfuran-2-yl)-4-oxobut-2-enoate $^{1}$H NMR ($d_1$-chloroform) δ 7.40 (d, 1, Ar), 7.10 (d, 1, Ar), 6.89 (s, 1, CH), 3.97 (s, 3, $CH_3$), 2.42 (s, 3, $CH_3$).

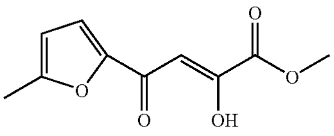

(Z)-2-hydroxy-4-(5-methylfuran-2-yl)-4-oxobut-2-enoic acid $^{1}$H NMR ($d_1$-chloroform) δ 7.40 (d, 1, Ar), 7.10 (d, 1, Ar), 6.89 (s, 1, CH), 2.42 (s, 3, $CH_3$).

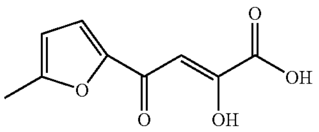

(Z)-methyl 4-(furan-2-yl)-2-hydroxy-4-oxobut-2-enoate $^{1}$H NMR ($d_1$-chloroform) δ 8.42 (d, 1, Ar), 8.02 (d, 1, Ar), 7.92 (t, 1, Ar), 6.91 (s, 1, CH), 3.97 (s, 3, $CH_3$).

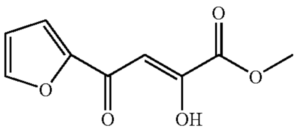

(Z)-4-(furan-2-yl)-2-hydroxy-4-oxobut-2-enoic acid $^{1}$H NMR ($d_1$-chloroform) δ 8.45 (d, 1, Ar), 8.05 (d, 1, Ar), 7.96 (t, 1, Ar), 6.97 (s, 1, CH).

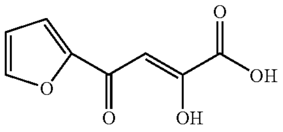 [SMILES: O=C(O)/C(O)=C/C(=O)c1ccco1]

(Z)-4-(benzofuran-2-yl)-2-hydroxy-4-oxobut-2-enoic acid $^{1}$H NMR ($d_1$-chloroform) δ 7.90 (d, 1, Ar), 7.71 (d, 1, Ar), 7.61 (s, 1, Ar), 7.40 (t, 1, Ar), 7.34 (t, 1, Ar), 6.90 (s, 1, CH).

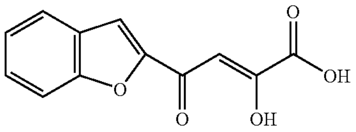 [SMILES: O=C(O)/C(O)=C/C(=O)c1cc2ccccc2o1]

(Z)-methyl 4-(5-(4-bromophenyl)thiophen-2-yl)-2-hydroxy-4-oxobut-2-enoate $^{1}$H NMR ($d_1$-chloroform) δ 8.00 (d, 2, Ar), 7.70 (d, 2, Ar), 7.59 (d, 2, Ar), 6.91 (s, 1, CH), 3.98 (s, 3, $CH_3$).

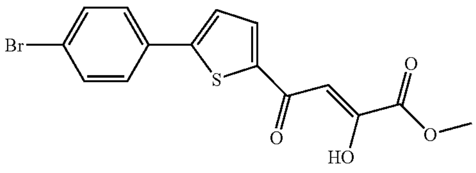 [SMILES: COC(=O)/C(O)=C/C(=O)c1ccc(-c2ccc(Br)cc2)s1]

(Z)-4-(5-(4-bromophenyl)thiophen-2-yl)-2-hydroxy-4-oxobut-2-enoic acid $^{1}$H NMR ($d_1$-chloroform) δ 8.01 (d, 2, Ar), 7.71 (d, 2, Ar), 7.60 (d, 2, Ar), 6.94 (s, 1, CH).

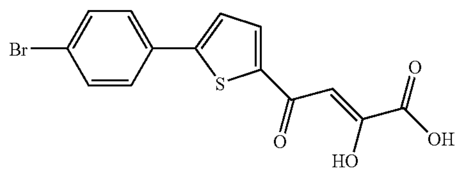 [SMILES: O=C(O)/C(O)=C/C(=O)c1ccc(-c2ccc(Br)cc2)s1]

(Z)-methyl 2-hydroxy-4-oxo-4-(pyridin-2-yl)but-2-enoate $^1$H NMR ($d_1$-chloroform) δ 8.68 (d, 1, Ar), 8.34 (d, 1, Ar), 7.92 (t, 1, Ar), 7.85 (t, 1, Ar), 6.95 (s, 1, CH), 3.98 (s, 3, $CH_3$).

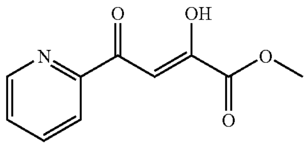

(Z)-2-hydroxy-4-oxo-4-(pyridin-2-yl)but-2-enoic acid $^1$H NMR ($d_1$-chloroform) δ 8.69 (d, 1, Ar), 8.35 (d, 1, Ar), 7.93 (t, 1, Ar), 7.87 (t, 1, Ar), 6.97 (s, 1, CH).

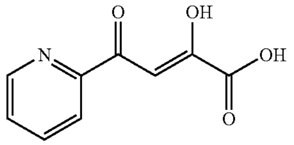

(Z)-methyl 2-hydroxy-4-oxo-4-(pyridin-4-yl)but-2-enoate $^1$H NMR ($d_1$-chloroform) δ 8.88 (d, 2, Ar), 8.01 (d, 2, Ar), 6.98 (s, 1, CH), 3.96 (s, 3, $CH_3$).

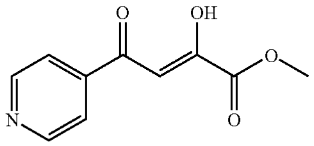

(Z)-2-hydroxy-4-oxo-4-(pyridin-4-yl)but-2-enoic acid $^1$H NMR ($d_1$-chloroform) δ 8.89 (d, 2, Ar), 8.05 (d, 2, Ar), 6.99 (s, 1, CH).

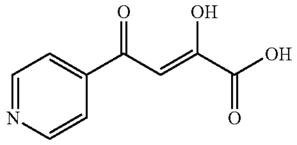 [SMILES: O=C(O)/C(O)=C/C(=O)c1ccncc1]

(Z)-methyl 2-hydroxy-4-oxo-4-(pyrimidin-2-yl)but-2-enoate $^1$H NMR ($d_1$-chloroform) δ 8.90 (d, 2, Ar), 8.23 (t, 1, Ar), 6.99 (s, 1, CH), 3.98 (s, 3, $CH_3$).

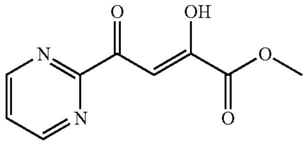

(Z)-2-hydroxy-4-oxo-4-(pyrimidin-2-yl)but-2-enoic acid $^1$H NMR ($d_1$-chloroform) δ 8.91 (d, 2, Ar), 8.24 (t, 1, Ar), 7.02 (s, 1, CH).

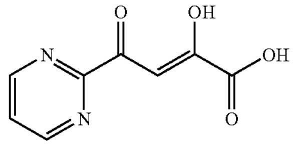 [SMILES: O=C(O)/C(O)=C/C(=O)c1ncccn1]

(Z)-methyl 2-hydroxy-4-oxo-4-(thiophen-3-yl)but-2-enoate $^1$H NMR ($d_1$-chloroform) δ 8.25 (s, 1, Ar), 7.77 (d, 1, Ar), 7.47 (d, 1, Ar), 6.98 (s, 1, CH), 3.94 (s, 3, $CH_3$).

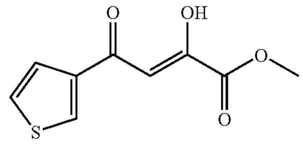

(Z)-2-hydroxy-4-oxo-4-(thiophen-3-yl)but-2-enoic acid $^1$H NMR ($d_1$-chloroform) δ 8.27 (s, 1, Ar), 7.78 (d, 1, Ar), 7.50 (d, 1, Ar), 6.99 (s, 1, CH).

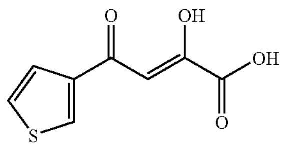 [SMILES: O=C(O)/C(O)=C/C(=O)c1ccsc1]

(Z)-tert-butyl 4-(2-bromophenyl)-2-hydroxy-4-oxobut-2-enoate $^1$H NMR ($d_1$-chloroform) δ 7.69 (d, 1, Ar), 7.58 (d, 1, Ar), 7.40 (t, 1, Ar), 7.26 (t, 1, Ar), 6.91 (s, 1, CH), 1.38 (s, 9, t-Bu).

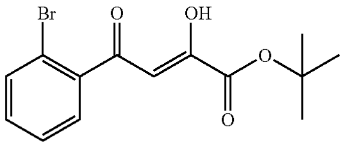 [SMILES: CC(C)(C)OC(=O)/C(O)=C/C(=O)c1ccccc1Br]

(Z)-benzyl 4-(2-bromophenyl)-2-hydroxy-4-oxobut-2-enoate $^1$H NMR ($d_1$-chloroform) δ 7.73 (d, 1, Ar), 7.70 (d, 1, Ar), 7.48-7.28 (m, 7, Ar), 6.93 (s, 1, CH), 5.37 (s, 2, $CH_2$).

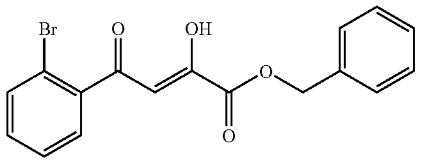 [SMILES: O=C(OCc1ccccc1)/C(O)=C/C(=O)c1ccccc1Br]

(Z)-methyl 4-(2-bromophenyl)-2-hydroxy-4-oxobut-2-enoate $^1$H NMR ($d_1$-chloroform) δ 7.69 (d, 1, Ar), 7.59 (d, 1, Ar), 7.39 (t, 1, Ar), 7.31 (t, 1, Ar), 6.91 (s, 1, CH), 3.92 (s, 3, $CH_3$).

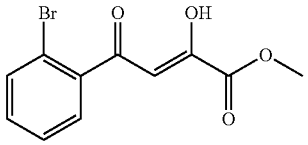 [SMILES: COC(=O)/C(O)=C/C(=O)c1ccccc1Br]

(Z)-4-(2-bromophenyl)-2-hydroxy-4-oxobut-2-enoic acid $^1$H NMR ($d_1$-chloroform) δ 7.70 (d, 1, Ar), 7.59 (d, 1, Ar), 7.41 (t, 1, Ar), 7.34 (t, 1, Ar), 7.11 (s, 1, CH).

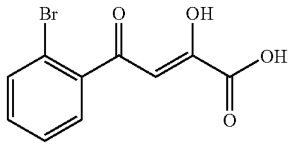 [SMILES: O=C(O)/C(O)=C/C(=O)c1ccccc1Br]

(Z)-tert-butyl 2-hydroxy-4-oxo-4-(o-tolyl)but-2-enoate $^1$H NMR ($d_1$-chloroform) δ 7.59 (d, 1, Ar), 7.40 (t, 1, Ar), 7.29 (t, 1, Ar), 7.21 (d, 1, Ar), 6.72 (s, 1, CH), 2.52 (s, 3, $CH_3$), 1.58 (s, 9, t-Bu).

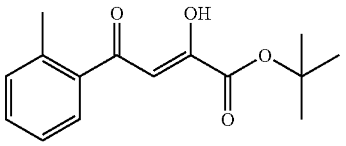 [SMILES: Cc1ccccc1C(=O)/C=C(\O)C(=O)OC(C)(C)C]

(Z)-benzyl 2-hydroxy-4-oxo-4-(o-tolyl)but-2-enoate $^1$H NMR ($d_1$-chloroform) δ 7.64 (d, 1, Ar), 7.60 (t, 1, Ar), 7.42-7.22 (m, 7, Ar), 6.81 (s, 1, CH), 5.37 (s, 2, $CH_2$), 2.51 (s, 3, $CH_3$).

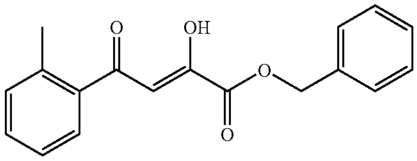 [SMILES: Cc1ccccc1C(=O)/C=C(\O)C(=O)OCc1ccccc1]

(Z)-methyl 2-hydroxy-4-oxo-4-(o-tolyl)but-2-enoate $^1$H NMR ($d_1$-chloroform) δ 7.64 (d, 1, Ar), 7.42 (t, 1, Ar), 7.31 (t, 1, Ar), 7.29 (d, 1, Ar), 6.87 (s, 1, CH), 3.95 (s, 3, $CH_3$), 2.57 (s, 3, $CH_3$).

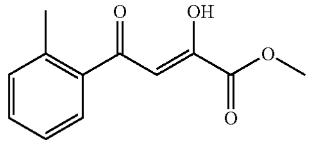 [SMILES: COC(=O)/C(O)=C/C(=O)c1ccccc1C]

(Z)-2-hydroxy-4-oxo-4-(o-tolyl)but-2-enoic acid $^1$H NMR ($d_1$-chloroform) δ 7.70 (d, 1, Ar), 7.48 (t, 1, Ar), 7.34 (t, 1, Ar), 7.31 (d, 1, Ar), 6.97 (s, 1, CH), 2.60 (s, 3, $CH_3$).

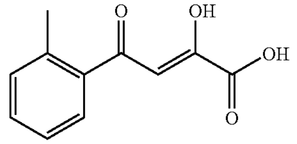

(Z)-methyl 2-hydroxy-4-oxo-4-phenyl but-2-enoate $^1$H NMR ($CDCl_3$) δ 8.02 (d, 2, Ar), 7.63 (t, 1, Ar), 7.53 (t, 2, Ar), 7.11 (s, 1, CH), 3.96 (s, 3, $OCH_3$).

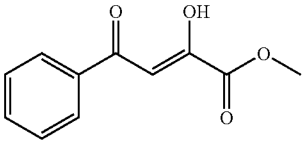

(Z)-ethyl 2-hydroxy-4-oxo-4-phenyl but-2-enoate $^1$H NMR ($CDCl_3$) δ 7.88 (m, 2, Ar), 7.52 (m, 1, Ar), 7.39 (t, 2, Ar), 6.98 (s, 1, CH), 4.30 (q, 2, $CH_2$), 1.31 (t, 3, $CH_3$).

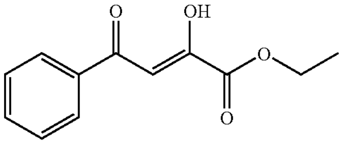 [SMILES: CCOC(=O)/C(O)=C/C(=O)c1ccccc1]

(Z)-2-hydroxy-4-oxo-4-phenylbut-2-enoic acid $^1$H NMR ($CD_3OD$) dδ 8.04 (d, 1, Ar), 7.62 (m, 1, Ar), 7.54 (t, 2, Ar), 7.13 (s, 1, CH).

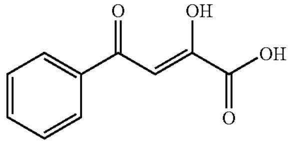 [SMILES: O=C(O)/C(O)=C/C(=O)c1ccccc1]

(Z)-methyl 2-hydroxy-4-(naphthalen-2-yl)-4-oxobut-2-enoate $^1$H NMR ($CDCl_3$) δ 15.3 (br s, 1, OH), 8.56 (s, 1, CH), 8.00 (m, 5, Ar), 7.62 (m, 2, Ar), 3.94 (s, 3, $OCH_3$).

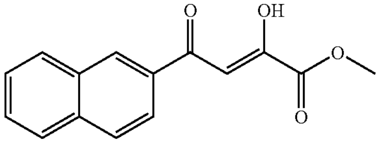 [SMILES: COC(=O)/C(O)=C/C(=O)c1ccc2ccccc2c1]

(Z)-2-hydroxy-4-(naphthalen-2-yl)-4-oxobut-2-enoic acid $^1$H NMR ($CD_3OD$) δ 8.56 (s, 1, Ar), 7.98 (m, 2, Ar), 7.90 (m, 2, Ar), 7.61 (m, 1, Ar), 7.56 (m, 1, Ar), 7.23 (s, 1, CH), 4.94 (br s, 1, OH).

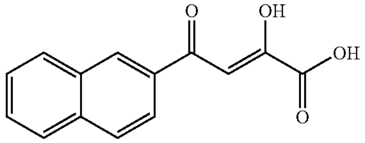 [SMILES: O=C(O)/C(O)=C/C(=O)c1ccc2ccccc2c1]

(Z)-methyl 2-hydroxy-4-(naphthalen-1-yl)-4-oxobut-2-enoate $^1$H NMR ($CDCl_3$) δ 15.1 (s, 1, OH), 8.61 (d, 2, Ar), 8.06 (d, 1, Ar), 7.92 (d, 1, Ar), 7.61 (m, 3, Ar), 7.03 (s, 1, CH), 3.97 (s, 3, $OCH_3$).

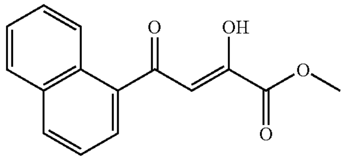 [SMILES: COC(=O)/C(O)=C/C(=O)c1cccc2ccccc12]

(Z)-2-hydroxy-4-(naphthalen-1-yl)-4-oxobut-2-enoic acid $^1$H NMR ($CD_3OD$) δ 8.48 (d, 1, Ar), 7.94 (d, 1, Ar), 7.82 (d, 1, Ar), 7.77 (d, 1, Ar), 7.47 (m, 2, Ar), 7.41 (t, 1, Ar), 6.89 (s, 1, CH).

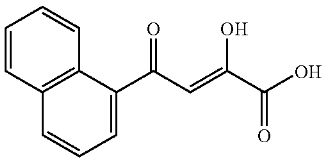 [SMILES: O=C(O)/C(O)=C/C(=O)c1cccc2ccccc12]

(Z)-methyl 4-(4-bromophenyl)-2-hydroxy-4-oxobut-2-enoate $^1$H NMR ($CDCl_3$) δ 15.2 (s, 1, OH), 7.87 (d, 2, Ar), 7.66 (d, 2, Ar), 7.05 (s, 1, CH), 3.96 (s, 3, $OCH_3$).

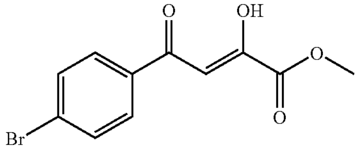 [SMILES: COC(=O)/C(O)=C/C(=O)c1ccc(Br)cc1]

(Z)-4-(4-bromophenyl)-2-hydroxy-4-oxobut-2-enoic acid $^1$H NMR ($CD_3OD$) δ 7.91 (d, 2, Ar), 7.68 (d, 2, Ar), 7.09 (s, 1, CH).

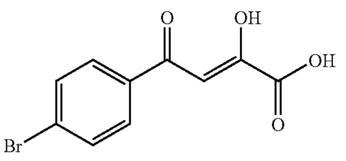 [SMILES: O=C(O)/C(O)=C/C(=O)c1ccc(Br)cc1]

(Z)-2-hydroxy-4-oxo-4-(4-propylphenyl)but-2-enoic acid $^1$H NMR ($CD_3OD$) δ 7.90 (d, 2, Ar), 7.31 (d, 2, Ar), 7.07 (s, 1, CH), 2.64 (t, 2, $CH_2$), 1.64 (m, 2, $CH_2$), 0.93 (t, 3, $CH_3$).

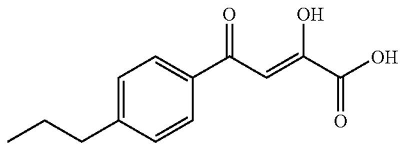 [SMILES: CCCc1ccc(C(=O)/C=C(\O)C(=O)O)cc1]

(Z)-4-(4-ethylphenyl)-2-hydroxy-4-oxobut-2-enoic acid $^1$H NMR ($CD_3OD$) δ 7.91 (44, 2, Ar), 7.33 (d, 2, Ar), 7.07 (s, 1, CH), 2.70 (q, 2, $CH_2$), 1.23 (t, 3, $CH_3$).

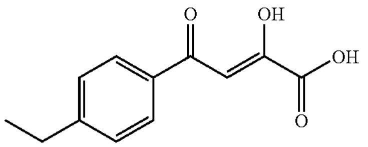 [SMILES: CCc1ccc(C(=O)/C=C(\O)C(=O)O)cc1]

(Z)-2-hydroxy-4-oxo-4-(4-benzylphenyl)but-2-enoic acid $^1$H NMR ($CD_3OD$) δ 7.92 (d, 2, Ar), 7.34 (d, 2, Ar), 7.27 (m, 2, Ar), 7.20 (m, 3, Ar), 7.08 (s, 1, CH), 4.00 (s, 2, $CH_2$).

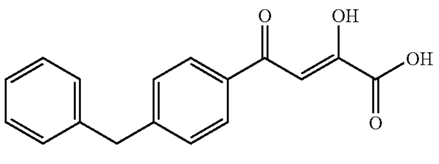 [SMILES: O=C(O)/C(O)=C/C(=O)c1ccc(Cc2ccccc2)cc1]

(Z)-methyl 4-(2-chloro-6-fluorophenyl)-2-hydroxy-4-oxobut-2-enoate $^1$H NMR ($CDCl_3$) δ 7.33 (q, 1, Ar), 7.20 (d, 1, Ar), 7.03 (t, 1, Ar), 6.61 (s, 1, CH), 3.74 (s, 3, $CH_3$).

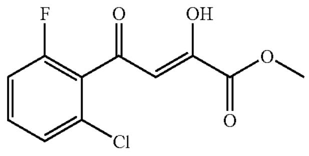 [SMILES: COC(=O)/C(O)=C/C(=O)c1c(F)cccc1Cl]

(Z)-methyl 4-(2-chloro-6-fluoro-3-methylphenyl)-2-hydroxy-4-oxobut-2-enoate $^1$H NMR ($CDCl_3$) δ 14.0 (s, 1, OH), 7.32 (t, 1, Ar), 7.01 (t, 1, Ar), 6.66 (s, 1, CH), 3.94 (s, 3, $CH_3$), 2.39 (s, 3, $CH_3$).

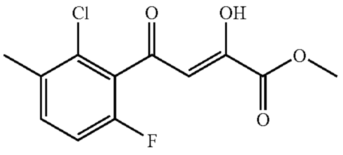

(Z)-4-(2-chloro-6-fluorophenyl)-2-hydroxy-4-oxobut-2-enoic acid $^1$H NMR ($CD_3OD$) δ 7.49 (m, 1, Ar), 7.35 (d, 1, Ar), 7.22 (m, 1, Ar).

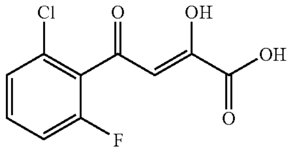

(Z)-4-(2-chloro-6-fluoro-3-methylphenyl)-2-hydroxy-4-oxobut-2-enoic acid $^1$H NMR ($CD_3OD$) δ 7.44 (m, 1, Ar), 7.11 (t, 1, Ar), 2.38 (s, 3, $CH_3$).

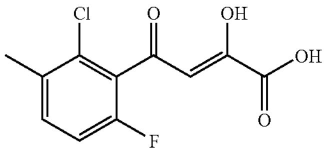 [SMILES: Cc1ccc(F)c(C(=O)/C=C(\O)C(=O)O)c1Cl]

Example 4

2-Substituted PKBA Analogs Achieve Whole-Cell Efficacy in Part Through Enhanced Stability Small halogens, particularly F, Cl, and Br, demonstrated significant improvements in GlcB inhibition, with the 2-fluoro compound exhibiting an $IC_{50}$=320 nM. The whole-cell activities of these compounds, and the 2-methyl derivative, all demonstrated growth inhibition of *M. smegmatis*

DglcBDgcl+*M. tuberculosis* glcB selectively on M9+acetate media that was significantly reduced (MIC>50-100 mM) upon overexpression of *M. tuberculosis* glcB (Table 1). These results provide substantial support that these compounds were specifically targeting GlcB.

Additionally, SAR holds in $mc^2$7000, with the most potent derivative (2-Br) exhibiting an MIC=6.2 mM on M9 media+ acetate. The 2-Br phenylketo butanoic acid exhibited *M. tuberculosis* H37Rv growth inhibition (MIC=6.2 mM on acetate, 12.5 mM on glucose) and demonstrated activity in a CD1 mouse in vitro microsome assay, with a substantial $t_{1/2}$ (>30 min) and a comparatively low rate of clearance (<0.3 mL/min·g). The 2-methylphenyl diketo ethyl ester exhibited *M. tuberculosis* H37Rv growth inhibition (MIC=3.9 mM on acetate, MIC=12.5 mM on glucose) compared to parent acid. Thus, specific targeting of the GlcB enzyme discloses compounds with significant potency versus *M. tuberculosis* and has validated that GlcB is essential in Mtb. with acetate or dextrose as a carbon source.

Figure 6A:
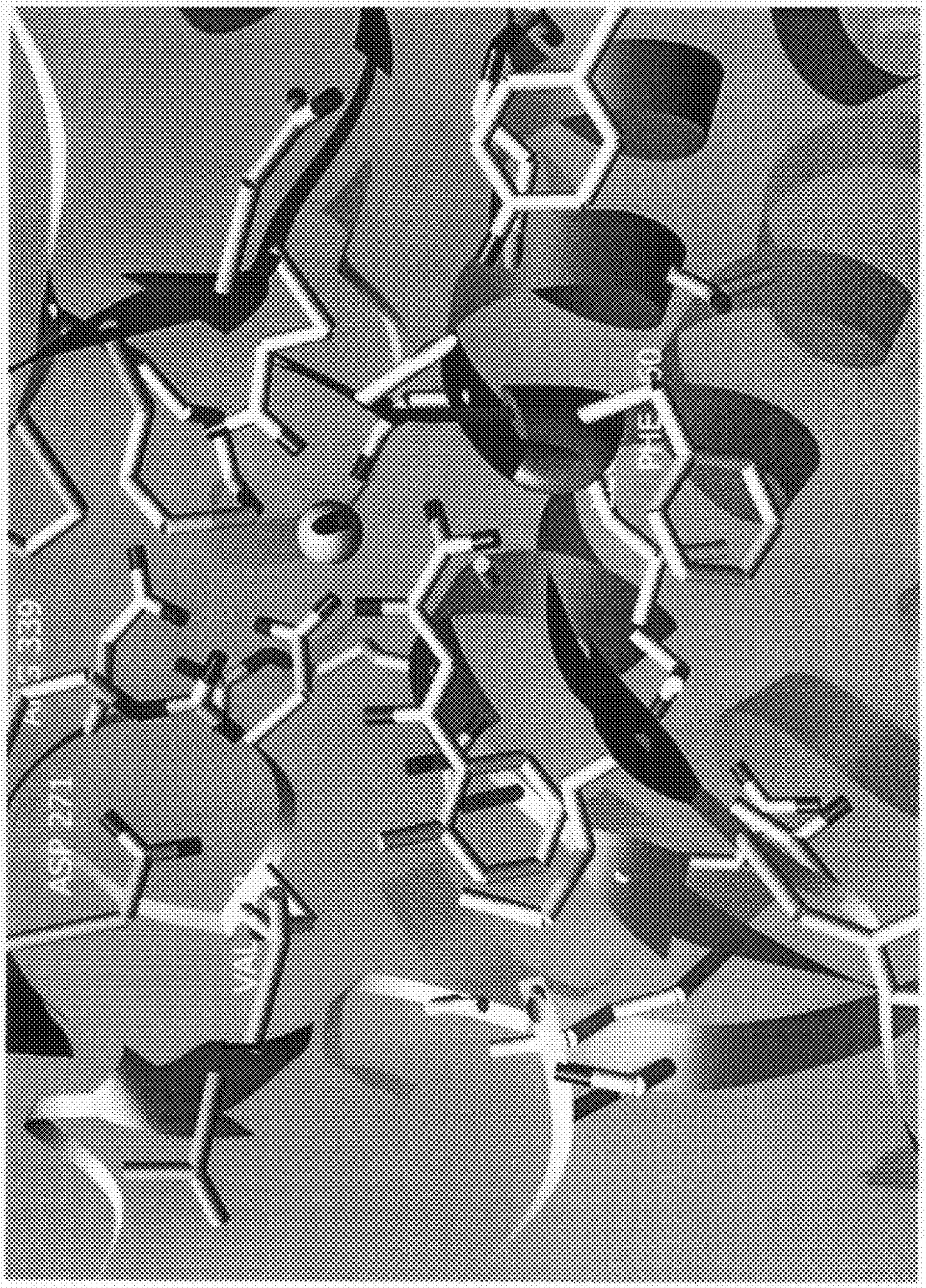
FIGS. 6A-6C show the superposition of docked ortho-substituted (FIG. 6A), meta-substituted (FIG. 6B) and para-substituted (FIG. 6C) phenyldiketo acids.
Figure 6B:
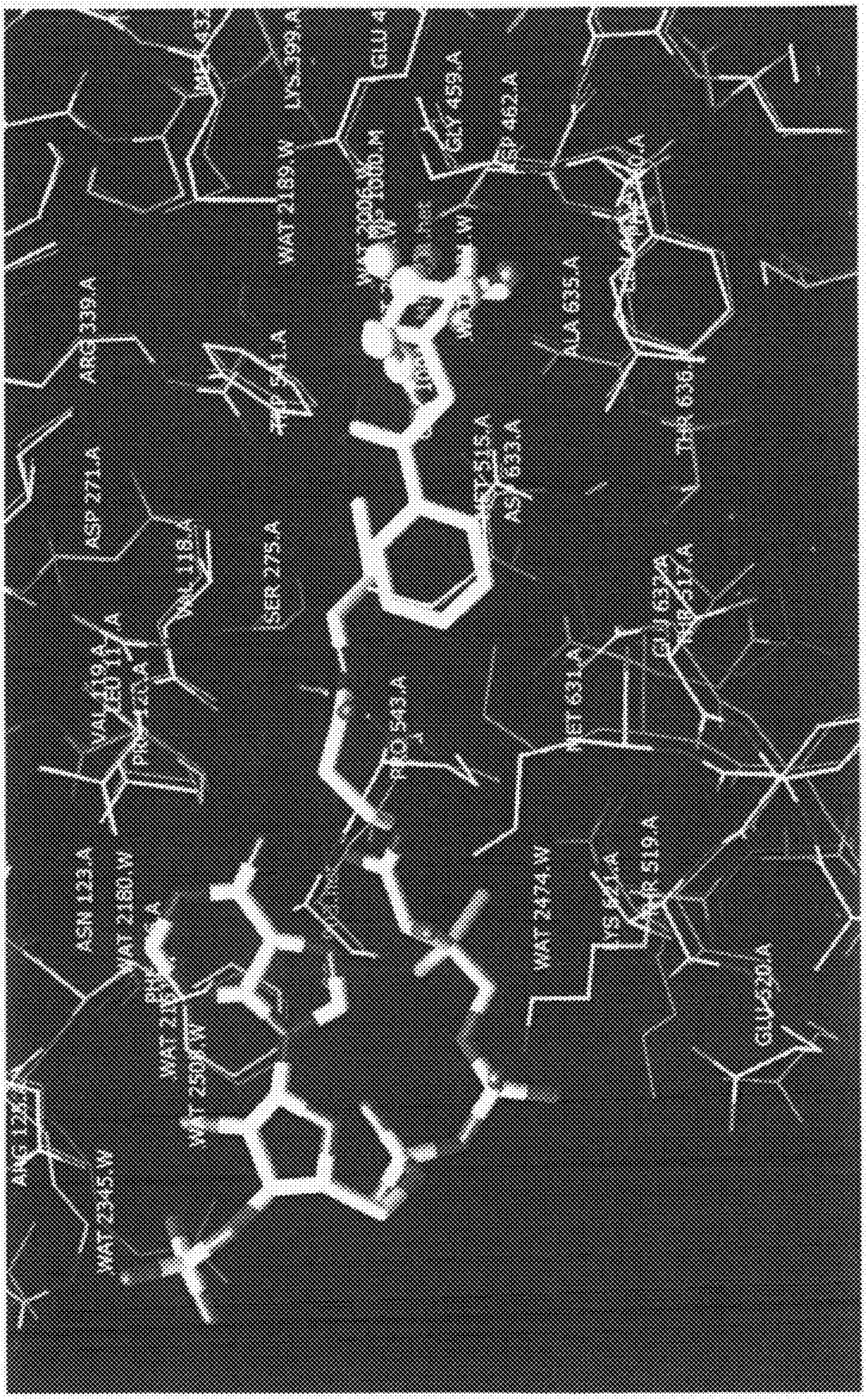
Figure 6C:
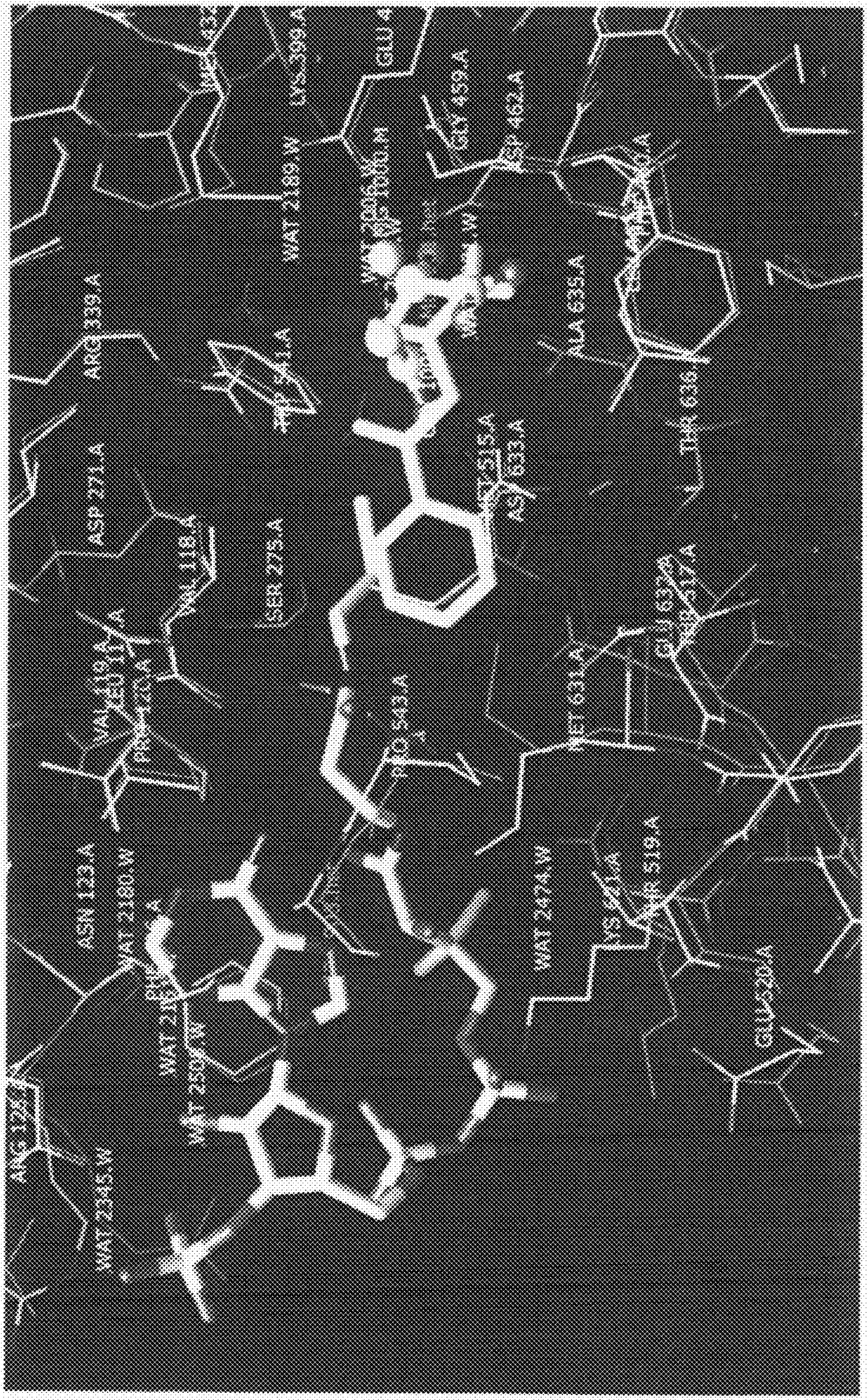

Table 1 presents results from the ortho-substituted phenyldiketo acids as inhibitors of the glyoxylate shunt in the *M. smegmatis* and *M. tuberculosis* models. Table 2 presents inhibition results from di- and tri-substituted phenyldiketo acids. Tables 3-4 present inhibition results from the meta- and para-substituted phenyldiketo acids as inhibitors of the glyoxylate shunt in the *M. smegmatis* models. Table 5 presents inhibition results from the substituted 2-thienyldiketo acid against the Mycobacterial models. None of the tested compounds demonstrated affinity for isocitrate lyase. FIGS. 6A-6C depict binding of the phenyldiketo acid structure within the active site of the malate synthase enzyme.

TABLE 1

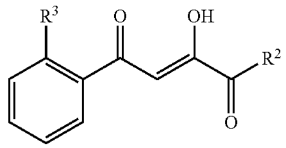

| | | | *M. smegmatis* MIC (μM) | | | | | | | |
|---|---|---|---|---|---|---|---|---|---|---|
| | | GlcB IC50 | GlcB | GlcB + Mtb glcB | + OE Mtb glcB | $mc^2$7000 MIC (μm) | | H37Rv MIC (μM) | | t½ |
| $R^3$ | $R^2$ | (μM) | 7H9 | M9 | M9 | 7H9 | M9 | glucose | acetate | (d) |
| H | OH | 4.0 | >100 | >50 | >50 | >50 | >50 | >50 | >50 | 3 |
| Me | OH | 8.6 | >100 | 12 | >100 | >100 | <3.1 | 31 | 8 | 30 |
| Et | OH | 37 | 100 | 50 | >100 | 100 | <3.1 | <3.1 | nt | 32 |
| n-Pr | OH | >50 | >100 | 100 | nt | >100 | >100 | nt | nt | nt |
| i-Pr | OH | >50 | >100 | 12 | >100 | >100 | <3.1 | nt | nt | 27 |
| F | OH | 0.32 | >100 | 3.1 | >100 | >100 | <3.1 | >100 | 50 | 12 |
| Cl | OH | 0.48 | >100 | 50 | >100 | >100 | >100 | nt | nt | 25 |
| Br | OH | 2.0 | >100 | 12 | >100 | 12.5 | <3.1 | 12.5 | 6.2 | 18 |
| I | OH | 3.3 | >50 | 12 | >50 | >100 | 50 | nt | nt | nt |
| $NO_2$ | OH | 2.6 | >100 | >100 | nt | nt | nt | nt | nt | nt |
| 2,4-Me | OH | 5.9 | 100 | 12 | >100 | >100 | <3.1 | nt | nt | nt |
| 2,5-Me | OH | 15 | >100 | 3.1 | >100 | >100 | <3.1 | nt | nt | nt |
| Me | OMe | 0% 50 μM cmpd | >50 | 3.1 | 50 | >100 | >100 | >125 | >125 | nt |
| Me | $OCH_2Ph$ | nt | nt | <3.1 | 25 | nt | nt | nt | nt | nt |
| Me | OEt | 19% 50 μM cmpd | >50 | 3.1 | 50 | 50 | 12.5 | 8.0 | 3.9 | nt |
| Me | Ot-Bu | nt | >100 | 3.1 | 25 | nt | nt | nt | nt | nt |
| OMe | OH | 0% 50 μM cmpd | >100 | >100 | nt | nt | nt | nt | nt | nt |
| Br | $OCH_2Ph$ | nt | >100 | 1.1 | >100 | nt | nt | nt | nt | nt |
| Br | Ot-Bu | nt | >100 | 3.1 | 100 | nt | nt | nt | nt | nt |
| Br | OMe | nt | >100 | 12 | >100 | 50 | 100 | 31 | 16 | nt |

TABLE 2

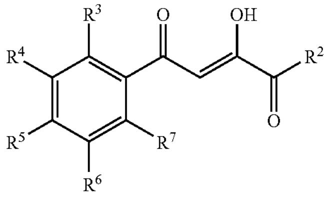

| | | | | M. smegmatis MIC (μM) | | | | | | |
|---|---|---|---|---|---|---|---|---|---|---|
| | | | GlcB IC50 | GlcB | GlcB + Mtb glcB | + OE Mtb glcB | $mc^2$ 7000 MIC (μm) | | H37Rv MIC (μM) | |
| $R^3$ | $R^4$—$R^7$ | $R^2$ | (μM) | 7H9 | M9 | M9 | 7H9 | M9 | glucose | acetate |
| Me | 3-Me | H | 5.9 | 100 | 12 | >100 | >100 | 25 | nt | nt |
| Me | 4-Me | H | 5.6 | >100 | 12 | 50 | >50 | 50 | >125 | >125 |
| Me | 4-Me | Me | 13% 50 μM cmpd | 100 | 6.2 | >100 | 25 | >50 | >125 | >125 |
| Me | 5-Me | H | 15 | 50 | 3.1 | >100 | >100 | 25 | >125 | >125 |
| Me | 5-Me | Me | 17% 50 μM cmpd | >100 | 3.1 | >100 | 12.5 | 50 | 62 | 24 |
| F | 5-F | H | 1.1 | >100 | >100 | >100 | nt | nt | nt | nt |
| F | 6-F | H | 5.0 | >100 | >100 | >100 | nt | nt | nt | nt |
| F | 4,5-F | H | 0% 50 μM cmpd | >100 | >100 | nt | nt | nt | nt | nt |
| F | 4,5-F | Me | | >100 | >100 | nt | nt | nt | nt | nt |
| F | 4,6-F | H | 0% 50 μM cmpd | >100 | >100 | nt | nt | nt | nt | nt |
| F | 4,6-F | Me | nt | >100 | >100 | nt | nt | nt | nt | nt |
| F | 3,4,5,6-F | H | 0% 50 μM cmpd | >100 | >100 | nt | nt | nt | nt | nt |
| F | 4-OMe | H | 3.0 | >100 | 50 | >100 | nt | nt | nt | nt |
| F | 5-OMe | H | 9.5 | >100 | 25 | >100 | nt | nt | nt | nt |
| F | 3-Me,6-Cl | Me | | >100 | 50 | nt | 6.2 | 50 | nt | nt |
| F | 3-Me,6-Cl | H | 7.3 | >100 | 50 | nt | 6.2 | >100 | nt | nt |
| Br | 4-Cl | H | 1.5 | >100 | 50 | nt | nt | nt | nt | nt |
| Br | 4-Cl | Me | | >100 | 12.5 | nt | nt | nt | nt | nt |
| Br | 4-F | H | 0.81 | >100 | 50 | nt | nt | nt | nt | nt |
| Br | 4-F | Me | | >100 | >12.5 | nt | nt | nt | nt | nt |
| Cl | 4-Cl | H | 1.4 | 100 | 25 | >100 | >100 | >100 | nt | nt |
| Cl | 4-Cl | Me | | 100 | 12.5 | >100 | >100 | >100 | nt | nt |
| Cl | 5-Cl | H | 4.9 | >100 | 25 | >100 | >100 | >100 | nt | nt |
| Cl | 5-Cl | Me | | 100 | 12.5 | >100 | >100 | >100 | nt | nt |
| Cl | 6-Cl | H | 0.51 | >100 | >100 | >100 | nt | nt | nt | nt |
| Cl | 6-Cl | Me | | >100 | >100 | >100 | nt | nt | 125 | 62 |
| Cl | 6-F | Me | | >100 | 50 | nt | nt | nt | nt | nt |
| Cl | 6-F | H | 1.2 | >100 | >100 | nt | 12 | 25 | nt | nt |
| Cl | 6-F,3-Me | Me | | >100 | 25 | nt | 6.2 | 12 | 8 | 4 |
| Cl | 6-F,3-Me | H | 7.0 | >100 | 50 | nt | 3.1 | 25 | 16 | 8 |

TABLE 3

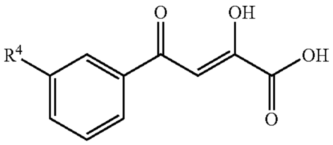

| | | M. smegmatis MIC (μM) | | |
|---|---|---|---|---|
| R4 | % inhibition w/1 μM cmpd | GlcB 7H9 | GlcB + Mtb glcB M9 | + OE Mtb glcB M9 |
| H | 41 | >50 | >50 | >50 |
| Me | 73 | >50 | 6.2 | 25 |
| CF3 | 10 | >100 | 25 | nt |
| Et | 72 | >50 | 6.2 | 6.2 |
| Br | 72 | >50 | 3.1 | 25 |
| Ph | 11 | >100 | 100 | nt |

TABLE 4

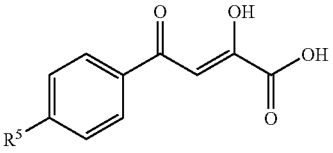

| | | M. smegmatis MIC (μM) | | |
|---|---|---|---|---|
| R5 | % inhibition w/1 μM cmpd | GlcB 7H9 | GlcB + Mtb glcB M9 | + OE Mtb glcB M9 |
| H | 41 | >50 | >50 | >50 |
| Me | 34 | >50 | 50 | 50 |
| Et | 57 | >50 | 12 | >50 |
| n-Pr | 31 | >50 | 25 | >50 |
| n-Bu | 37 | >50 | 50 | 50 |
| Ph | 11 | >50 | >50 | >50 |

TABLE 4-continued

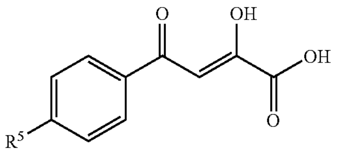

| R5 | % inhibition w/1 μM cmpd | *M. smegmatis* MIC (μM) GlcB 7H9 | GlcB + Mtb glcB M9 | + OE Mtb glcB M9 |
|---|---|---|---|---|
| $PhCH_2$ | 0 | >100 | 100 | nt |
| $Ph(CH_2)_2$ | 0 | >100 | >100 | nt |
| Br | 23 | >50 | 6.2 | >100 |
| 1-naphthyl ($R^5Ph$) | 18 | >100 | 1.6 | 100 |
| 2-naphthyl ($R^5Ph$) | 68 | >50 | 25 | 50 |

TABLE 5

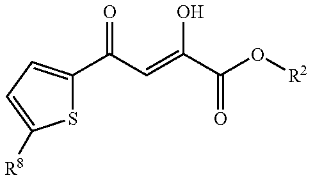

| | | GlcB IC50 | *M. smegmatis* MIC (μM) GlcB | GlcB + Mtb glcB | + OE Mtb glcB | mc²7000 MIC (μm) | | t½ |
|---|---|---|---|---|---|---|---|---|
| $R^8$ | $R^2$ | (μM) | 7H9 | M9 | M9 | 7H9 | M9 | (d) |
| 2-thienyl | H | 0.17 | >100 | 25 | >50 | 12.5 | >100 | 14 |
| 2-thienyl | Me | nt | >100 | 1.6 | 50 | 12.5 | 50 | 14 |
| p-FPh | H | 0.24 | 100 | 3.1 | >25 | 25 | 12 | 14 |
| p-FPh | Me | nt | >100 | 6.2 | 12 | <3.1 | <3.1 | 14 |
| p-ClPh | H | 0.12 | 100 | 25 | 50 | nt | nt | 12 |
| p-ClPh | Me | nt | 100 | 50 | 100 | nt | nt | 13 |
| p-BrPh | H | 0.080 | 100 | 25 | 50 | nt | nt | 12 |
| p-BrPh r | Me | nt | 100 | 100 | 100 | nt | nt | 13 |
| p-OHPh | H | 0.22 | 100 | >100 | >100 | nt | nt | 9 |
| p-OHPh | Me | nt | >100 | 50 | 100 | nt | nt | 9 |
| p-OMePh | H | 0.14 | >100 | 6.2 | >100 | <3.1 | <3.1 | 14 |
| p-OMePh | Me | nt | >100 | 12 | 100 | >100 | 50 | 14 |
| p-OPhPh | H | 17 | 6.2 | 50 | 50 | nt | nt | nt |
| p-OPhPh | Me | nt | <3.1 | 25 | 25 | nt | nt | nt |
| Ph(3-Me) | H | 0.38 | >100 | 1.1 | 100 | 12 | 6.2 | 20 |
| Ph(3-Me) | Me | nt | >100 | <3.1 | 25 | nt | nt | 20 |

Example 5

Modification of the Aryl Ring in PKBA Affords Potent GlcB Inhibitors

PKBA exhibits an $IC_{50}$=4.0 μM versus GlcB. However, PKBA failed to show significant whole-cell activity because of a lack of stability in a buffered solution. PKBA was stable in water or DMSO, but unstable in buffer (20 mM TrisHCl, +5 mM $MgCl_2$+0.8 mM EDTA@pH 7.5) with a half-life ($t_{1/2}$) of 3 days. The decomposition most likely occurs through a retro-Claisen reaction that has been documented only once in the literature despite the prevalence of phenyldiketo acids as hits versus HIV-1 integrase and HCV polymerase enzymes.

Figure 7:
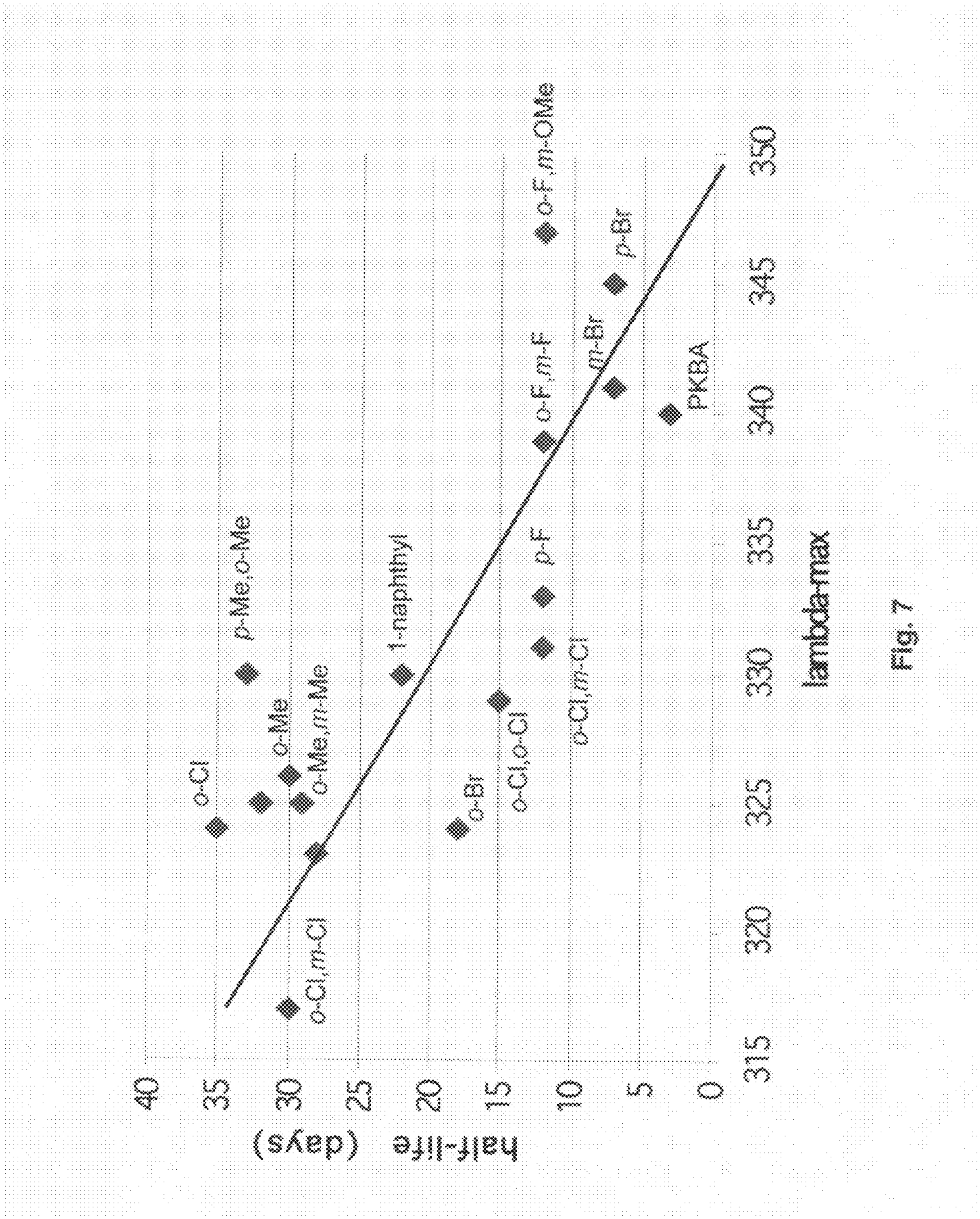
FIG. 7 illustrates the correlation between absorbance peaks and stability in solution in selected phenyl-substituted or napthyl keto butanoic acid derivatives and analogs.

Thus solution-phase stability appears to be a limiting factor with PKBA in whole-cell testing. It was dramatically improved in analogs with a 2-substituted phenyl moiety, with $t_{1/2}$ values ranging typically from 12 to 36 days (FIG. 7). It is contemplated that the 2-substituent perturbs the relative orientation of the aromatic ring with the diketoacid moiety, disfavoring the retro-Claisen decomposition. This movement of the aromatic ring out of coplanarity with the diketo acid is substantiated by X-ray crystallography and UV/Vis$_{—max}$ measurements, as an overall measure of a molecule's degree of conjugation. Substitutions at the 2-position show that stability of PKBA analogs was improved, and these acid containing compounds indeed show increased whole-cell activity. Importantly, this same effect is witnessed in the 2-thiophenediketo acid series. As shown in Table 5, compounds without a 3-substituent (ortho- to the diketoacid/ester substituent) display a solution-phase stability $t_{1/2}$ of 9-14 d. Installation of a 3-methyl group affords molecules with t1/2=20 d, via inhibiting the retro-Claisen decomposition.

The following references are cited herein:

1. Smith et al. J. Biol. Chem., 278(2):1735-1743, Jan. 17, 2003.
2. Hazuda et al., Proc Natl Acad Sci USA, 97(21):11244-9 (Oct. 10, 2003).

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A substituted diketo acid compound with the chemical structure:

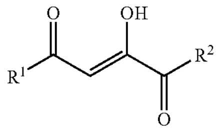

wherein $R^1$ is phenyl substituted with one or more of $R^3$ at C2, $R^4$ at C3, $R^5$ at C4, $R^6$ at C5, or $R^7$ at C6, wherein $R^3$, $R^4$, $R^5$, $R^6$, and $R^7$ independently are H, Br, F, Cl, I, O($C_{1-6}$alkyl), ($C_{1-6}$alkyl), dioxopyrrolyl, $Ph(CH_2)_2$, $CF_3$, imidazolyl, or methylsulfonyl, wherein two or more of $R^3$, $R^4$, $R^5$, $R^6$ or $R^7$ are independently $OCH_3$, Br, F, Cl, I, or $CH_3$, or wherein $R^1$ is a 1- or 2-naphthyl substituted with one or more of $R^3$ at C3, $R^4$ at C4, $R^5$ at C5, wherein $R^3$ and $R^4$ are H, and $R^5$ is $OC_{1-6}$ alkoxy; and $R^2$ is OH or $OC_{1-6}$alkyl; or a pharmacologically acceptable salt thereof.

2. A pharmaceutical composition comprising the substituted diketo acid compound of claim 1 and a pharmaceutically acceptable carrier.

3. A method for inhibiting an activity of a malate synthase enzyme in a bacterium, comprising:

contacting the bacterium with an effective amount of the compound of claim 1.

4. The method of claim 3, wherein the bacterium is a *Mycobacterium*.

5. The method of claim 4, wherein the *Mycobacterium* is *Mycobacterium tuberculosis*.

6. A method for treating tuberculosis in a subject, comprising:

administering one or more times a pharmacologically effective amount of one or more of the compounds of claim 1 to the subject.

7. The method of claim 6, further comprising:

administering one or more times a pharmacologically effective amount of one or more other tuberculosis drugs.

8. The method of claim 7, wherein the other tuberculosis drugs are isoniazid, rifampicin, pyrazinamide, or ethambutol.

9. The method of claim 7, wherein the other tuberculosis drugs are administered concurrently or consecutively.

10. A method for treating tuberculosis in a subject, comprising:

administering one or more times a pharmacologically effective amount of one or more of the substituted diketo acid compounds of claim 1 and one or more other tuberculosis drugs that are isoniazid, rifampicin, pyrazinamide, or ethambutol to the subject.

11. The method of claim 10, wherein the other tuberculosis drugs are administered concurrently or consecutively with the substituted diketo acid compounds.

12. A substituted diketo acid compound selected from the group consisting of (Z)-4-(2,5-difluorophenyl)-2-hydroxy-4-oxobut-2-enoic acid, (Z)-4-(2-fluoro-5-methoxyphenyl)-2-hydroxy-4-oxobut-2-enoic acid, (Z)-4-(2-fluoro-4-methoxyphenyl)-2-hydroxy-4-oxobut-2-enoic acid, (Z)-4-(2,6-dichlorophenyl)-2-hydroxy-4-oxobut-2-enoic acid, (Z)-methyl 4-(2,4-difluorophenyl)-2-hydroxy-4-oxobut-2-enoate, (Z)-4-(2,4-difluorophenyl)-2-hydroxy-4-oxobut-2-enoic acid, (Z)-methyl 4-(2,5-dichlorophenyl)-2-hydroxy-4-oxobut-2-enoate, (Z)-4-(2,5-dichlorophenyl)-2-hydroxy-4-oxobut-2-enoic acid, (Z)-methyl 4-(3,5-difluorophenyl)-2-hydroxy-4-oxobut-2-enoate, (Z)-4-(3,5-difluorophenyl)-2-hydroxy-4-oxobut-2-enoic acid, (Z)-methyl 4-(2,4-dichlorophenyl)-2-hydroxy-4-oxobut-2-enoate, (Z)-4-(2,4-dichlorophenyl)-2-hydroxy-4-oxobut-2-enoic acid, (Z)-methyl 4-(2,6-difluorophenyl)-2-hydroxy-4-oxobut-2-enoate, (Z)-4-(2,6-difluorophenyl)-2-hydroxy-4-oxobut-2-enoic acid, (Z)-methyl 2-hydroxy-4-oxo-4-(perfluorophenyl)but-2-enoate, (Z)-2-hydroxy-4-oxo-4-(perfluorophenyl)but-2-enoic acid, (Z)-methyl 2-hydroxy-4-oxo-4-(2,4,5-trifluorophenyl)but-2-enoate, (Z)-2-hydroxy-4-oxo-4-(2,4,5-trifluorophenyl)but-2-enoic acid, (Z)-methyl 4-(2-bromo-4-chlorophenyl)-2-hydroxy-4-oxobut-2-enoate, (Z)-4-(2-bromo-4-chlorophenyl)-2-hydroxy-4-oxobut-2-enoic acid, (Z)-4-(3,5-d ibromo-4-hydroxyphenyl)-2-hydroxy-4-oxobut-2-enoic acid, (Z)-methyl 4-(2-bromo-4-fluorophenyl)-2-hydroxy-4-oxobut-2-enoate, (Z)-4-(2-bromo-4-fluorophenyl)-2-hydroxy-4-oxobut-2-enoic acid, (Z)-m ethyl 2-hydroxy-4-oxo-4-(2,4,6-trifluorophenyl)but-2-enoate, (Z)-2-hydroxy-4-oxo-4-(2,4,6-trifluorophenyl)but-2-enoic acid, (Z)-methyl 2-hydroxy-4-(4-(methylsulfonyl)phenyl)-4-oxobut-2-enoic acid, (Z)-methyl 4-(4-(1H-imidazol-1-yl)phenyl)-2-hydroxy-4-oxobut-2-enoate, (Z)-4-(4-(1H-imidazol-1-yl)phenyl)-2-hydroxy-4-oxobut-2-enoic acid, (Z)-methyl-4-(4-(2,5-dioxo-2,5-dihydro-1H-pyrrol-1-yl)phenyl)-2-hydroxy-4-oxobut-2-enoate, (Z)-4-(4-(2,5-dioxo-2,5-dihydro-1H-pyrrol-1-yl)phenyl)-2-hydroxy-4-oxobut-2-enoic acid, (Z)-methyl 4-(6-chloro-2-fluoro-3-methyl phenyl)-2-hydroxy-4-oxobut-2-enoate, (Z)-4-(6-chloro-2-fluoro-3-methylphenyl)-2-hydroxy-4-oxobut-2-enoic acid, (Z)-tert-butyl 4-(2-bromophenyl)-2-hydroxy-4-oxobut-2-enoate, (Z)-benzyl 4-(2-bromophenyl)-2-hydroxy-4-oxobut-2-enoate, (Z)-methyl 4-(2-bromophenyl)-2-hydroxy-4-oxobut-2-enoate, (Z)-4-(2-bromophenyl)-2-hydroxy-4-oxobut-2-enoic acid, (Z)-tert-butyl 2-hydroxy-4-oxo-4-(o-tolyl)but-2-enoate, (Z)-benzyl 2-hydroxy-4-oxo-4-(o-tolyl)but-2-enoate, (Z)-4-(4-bromophenyl)-2-hydroxy-4-oxobut-2-enoic acid, (Z)-2-hydroxy-4-oxo-4-(4-propylphenyl)but-2-enoic acid, (Z)-4-(4-ethylphenyl)-2-hydroxy-4-oxobut-2-enoic acid, (Z)-methyl 4-(2-chloro-6-fluorophenyl)-2-hydroxy-4-oxobut-2-enoate, (Z)-methyl 4-(2-chloro-6-fluoro-3-methylphenyl)-2-hydroxy-4-oxobut-2-enoate, (Z)-4-(2-chloro-6-fluorophenyl)-2-hydroxy-4-oxobut-2-enoic acid, and (Z)-4-(2-chloro-6-fluoro-3-methylphenyl)-2-hydroxy-4-oxobut-2-enoic acid.

* * * * *